(12) United States Patent
Gonzalez et al.

(10) Patent No.: US 11,571,413 B2
(45) Date of Patent: Feb. 7, 2023

(54) NICOTINAMIDE RIBOSIDE TREATMENTS OF DOMESTICATED MEAT ANIMALS

(71) Applicant: Kansas State University Research Foundation, Manhattan, KS (US)

(72) Inventors: John Michael Gonzalez, Manhattan, KS (US); Stephanie Rene Kruger, Manhattan, KS (US); Chad Bennett Paulk, Manhattan, KS (US); Haley Kay Wecker, Manhattan, KS (US); Kara Dunmire, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 273 days.

(21) Appl. No.: 16/913,458

(22) Filed: Jun. 26, 2020

(65) Prior Publication Data

US 2021/0000808 A1 Jan. 7, 2021

Related U.S. Application Data

(63) Continuation-in-part of application No. PCT/US2018/067865, filed on Dec. 28, 2018.

(60) Provisional application No. 62/611,087, filed on Dec. 28, 2017.

(51) Int. Cl.
*A61K 31/443* (2006.01)
*A61K 9/00* (2006.01)

(52) U.S. Cl.
CPC .......... *A61K 31/443* (2013.01); *A61K 9/0019* (2013.01); *A61K 9/0053* (2013.01)

(58) Field of Classification Search
CPC .................................................. A61K 31/443
See application file for complete search history.

(56) References Cited

U.S. PATENT DOCUMENTS

2015/0056274 A1* 2/2015 Zemel ...................... A61P 3/06
514/210.02
2017/0204131 A1 7/2017 Szczepankiewicz et al.

FOREIGN PATENT DOCUMENTS

| CN | 105393976 | 3/2016 |
| WO | 2017062311 | 4/2017 |
| WO | 2017109195 | 6/2017 |

OTHER PUBLICATIONS

International Search Report and Written Opinion in corresponding PCT/US2018/067865, dated Mar. 27, 2019.

\* cited by examiner

*Primary Examiner* — Rei Tsang Shiao
(74) *Attorney, Agent, or Firm* — Hovey Williams LLP

(57) ABSTRACT

Described herein are methods of increasing meat quantity and/or improving meat quality of domesticated meat animals using treatments of nicotinamide riboside. The nicotinamide riboside may be in the form of a chloride salt mixed or dissolved in a biologically-acceptable carrier. The treatments may be provided as an in ovo injection or orally administered to the live domesticated meat animal. The methods described herein advantageously increase the size and weight of the domesticated meat animals, reduce the incidences of transportation fatigue, and decrease meat discoloration over time.

26 Claims, 19 Drawing Sheets

Specification includes a Sequence Listing.

NICOTINAMIDE RIBOSIDE TREATMENTS OF DOMESTICATED MEAT ANIMALS

CROSS-REFERENCE TO RELATED APPLICATION

This application is a continuation-in-part application of International Patent Application No. PCT/US18/67865, filed Dec. 28, 2018, entitled NICOTINAMIDE RIBOSIDE TREATMENTS OF DOMESTICATED MEAT ANIMALS, which claims the benefit of U.S. Provisional Application No. 62/611,087, filed Dec. 28, 2017, entitled NICOTINAMIDE RIBOSIDE TREATMENTS OF DOMESTICATED MEAT ANIMALS, each of which are incorporated by reference in their entirety herein.

STATEMENT REGARDING FEDERALLY SPONSORED RESEARCH OR DEVELOPMENT

This invention was made with government support under Contract No. NC-1184 and Contract No. NA/1006677, both awarded by the U.S. Department of Agriculture. The government has certain rights in the invention.

SEQUENCE LISTING

The following application contains a sequence listing in computer readable format (CRF), submitted as a text file in ASCII format entitled "Sequence Listing," created on Sep. 29, 2020, as 2 KB. The content of the CRF is hereby incorporated by reference.

BACKGROUND OF THE INVENTION

Field of the Invention

The invention is generally directed to methods of increasing meat quantity and/or improving meat quality of domesticated meat animals using treatments of nicotinamide riboside.

Description of the Prior Art

Nicotinamide riboside (NR) is a pyridine-nucleoside form of vitamin B3 that functions as a precursor to nicotinamide adenine dinucleotide, which can produce NAD+. Previous studies have found that NR enhances oxidative metabolism and protects against high-fat diet-induced obesity. Other studies have explored its effects on energy metabolism and neuroprotection. Other studies have explored the effect of NAD+ on slowing stem cell loss and aging. However, while previous studies have focused on the use of nicotinamide riboside for improving health, no one has explored its use in increasing meat quantity and/or improving meat quality in domesticated meat animals. Notably, no studies have been conducted that examine the effect of nicotinamide riboside on chicken myogenesis (muscle development) in utero or pig growth and meat quality.

SUMMARY OF THE INVENTION

Embodiments of the present invention demonstrate that an in ovo injection of nicotinamide riboside in developing chicken embryos increased the body weight, and weight, length, and depth of the Pectoralis major muscle of the chickens, and particularly of the chicks immediately after hatching. This may increase the efficiency and weight of birds produced for meat production. Other embodiments of the present invention demonstrate that nicotinamide riboside consumption by pigs increases growth, improves meat quality, and increases muscle NAD+ content. This increases the efficiency of growth, lengthens the time of retail meat sales, and may be used as a counter measure to delay the onset of transportation fatigue.

According to one embodiment, therefore, there is provided herein a method of increasing meat quantity and/or improving meat quality in a domesticated meat animal. The method comprises providing to the domesticated meat animal or to an embryo of the domesticated meat animal an effective amount of nicotinamide riboside.

DETAILED DESCRIPTION OF THE PREFERRED EMBODIMENT

Figure 1:
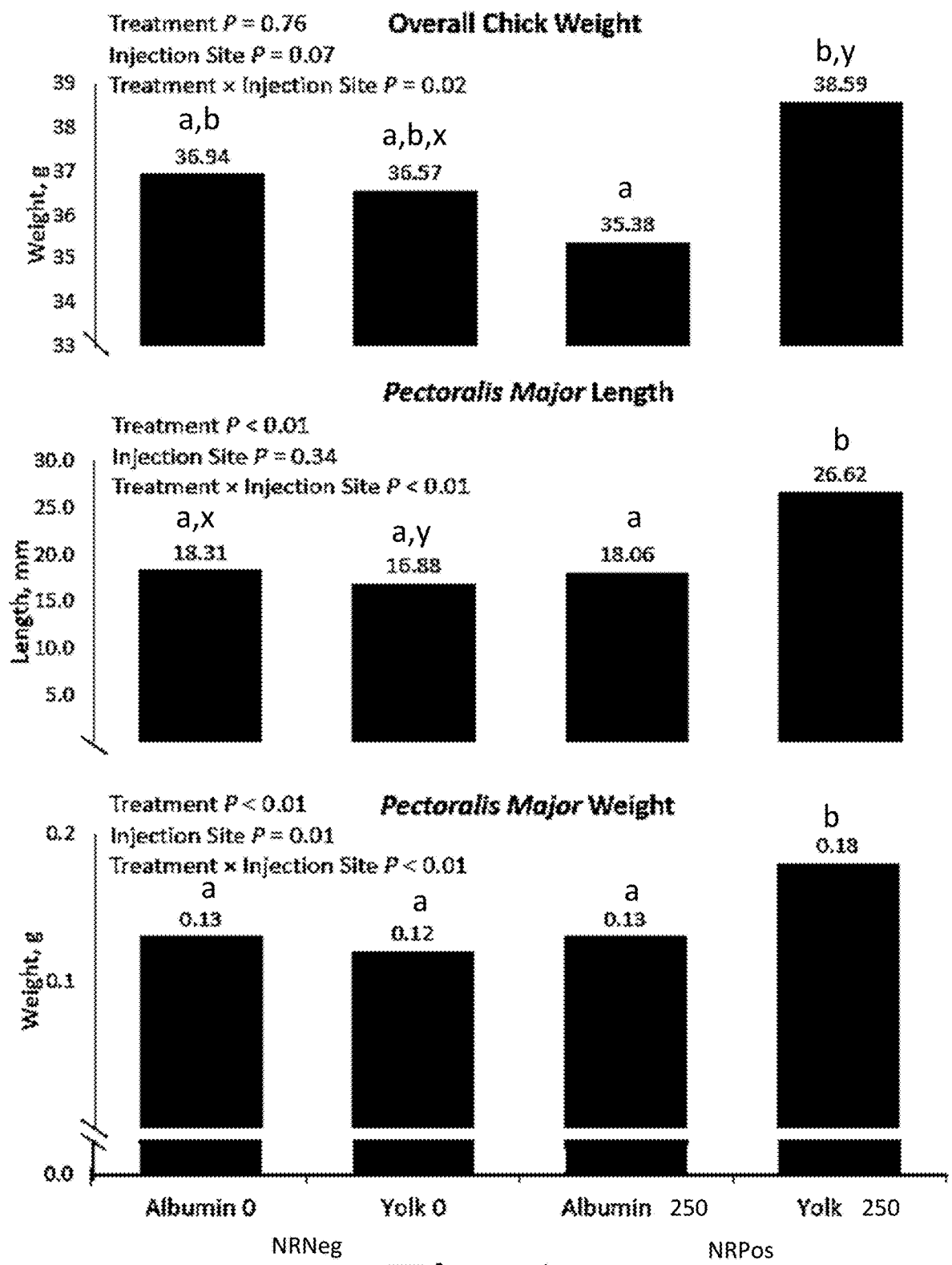
FIG. 1 is a series of graphs showing the effects on overall chick weight, and Pectoralis major length, weight, and depth of nicotinamide riboside treatments in accordance with embodiments of the present invention.
Figure 1:
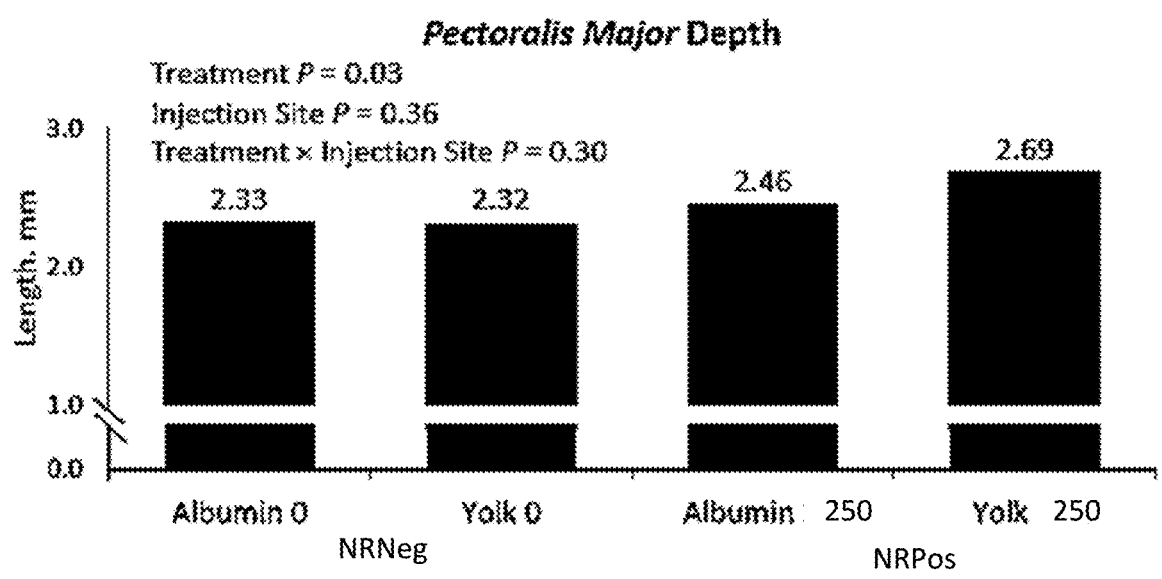

In one or more embodiments, there is provided a method of increasing meat quantity and/or improving the quality in a domesticated meat animal. As used herein, the term "domesticated meat animal" refers to animals that have been raised in captivity for consumption by people. Exemplary domesticated meat animals include birds, pigs, bovines, and the like. In certain preferred embodiments, the domesticated meat animal is a chicken (e.g., a broiler chicken) or a pig. Methods in accordance with embodiments of the present invention generally comprise providing to the domesticated meat animal or to an embryo of the domesticated meat animal an effective amount of nicotinamide riboside. Nicotinamide riboside (NR) is a pyridine-nucleoside form of vitamin $B_3$ that functions as a precursor to nicotinamide adenine dinucleotide, which can produce NAD+. The nicotinamide riboside is preferably provided to the domesticated meat animal as the salt nicotinamide riboside chloride. However, the nicotinamide riboside may also be provided in another biologically-acceptable form. For example, nicotinamide riboside may also be provided as nicotinamide riboside oxide, nicotinamide riboside sulfate, or combined with amino acid complexes.

In a particular embodiment, there is provided a method of increasing meat quantity of a chicken. The method comprises providing a chicken embryo with an effective amount of nicotinamide riboside. The nicotinamide riboside can be provided to the chicken embryo by injecting the nicotinamide riboside into a fertilized chicken egg during the incubation period. The injection is generally made about 10 days or more after the egg is laid and preferably about 10 to about 12 days after the egg is laid. In certain embodiments, and particularly when the egg is not incubated immediately after being laid, the injection may be made about 10 days or more after the beginning of egg incubation and preferably about 10 to about 12 days after the beginning of egg incubation. The injection is preferably made into the yolk (i.e., yolk sac) of the fertilized chicken egg. Injecting the nicotinamide riboside into the yolk sac can advantageously result in increased meat quantity of hatched chicks compared to injecting into other portions of the chicken egg, such as the albumen.

The injection generally comprises a quantity of nicotinamide riboside dissolved in a biologically-acceptable liquid carrier. For example, the liquid carrier can be a sterile saline solution. The volume of nicotinamide riboside injected into the fertilized egg can be varied. However, the injection generally comprises about 1 µl to about 1000 µl, preferably about 25 µl to about 500 µl, and more preferably about 50 µl to about 200 µl of solution, wherein the solution concentration is about 0.1 mM to about 10 mM, preferably about 1 mM to about 5 mM, and more preferably about 2 mM to about 3 mM of nicotinamide riboside. However, in certain embodiments, doses providing greater amounts of nicotinamide riboside may also be used. In certain embodiments, the concentration of nicotinamide riboside in the solution is at least about 2.5 mM, at least about 5 mM, at least about 7.5 mM, at least about 10 mM, at least about 50 mM, at least about 100 mM, or at least about 250 mM. In certain embodiments, the concentration of nicotinamide riboside in the solution is about 250 mM to about 1,000 mM. In certain embodiments, the concentration of nicotinamide riboside in the yolk (accounting for the volume of the yolk) is about 2.5 mM to about 10 mM. In certain embodiments, the injection is made into the chicken egg at a depth of about 0.5 cm to about 2 cm, preferably about 0.7 to about 1.5 cm, and more preferably about 0.9 to about 1.2 cm.

After injection, the fertilized chicken eggs are generally incubated under natural conditions (i.e., broody hen) or in an artificial environment. Regardless, the fertilized chicken eggs are incubated at a temperature of about 30° C. to about 40° C. and preferably about 34° C. to about 40° C., and a relative humidity of about 30% to about 50% and preferably about 38% to about 42%. In the final about 3 to about 5 days of incubation before hatching, the humidity may be increased to about 50% to about 70% and preferably about 58% to about 62%. The methods described herein can advantageously result in chicks having increased overall weight, as well as increased Pectoralis major muscle weight, length, and depth compared to untreated chicks.

In another particular embodiment, there is provided a method of increasing meat quantity and/or improving meat quality of a pig. The method comprises providing a pig with an effective amount of nicotinamide riboside. The pig may be an adult pig or piglet. The nicotinamide riboside can be provided to the pig by orally administering a quantity of nicotinamide riboside to the pig, although other methods of administering may also be used. The oral administration treatment comprises a quantity of nicotinamide riboside mixed with a biologically-acceptable carrier. The carrier is preferably in the form of a liquid or solid drink or foodstuff that has a desirable flavor to the pig. For example, the carrier may be corn syrup, such as Karo® dark syrup. Regardless the carrier, the nicotinamide riboside is generally administered to the pig at a dose of about 15 mg to about 30 mg of nicotinamide riboside per kg of body weight of the pig. In particularly preferred embodiments, the nicotinamide riboside is administered to the pig at a dose of about 30 mg of nicotinamide riboside per kg of body weight of the pig. However, in other preferred embodiments, the nicotinamide riboside is administered to the pig at a dose of about 15 mg of nicotinamide riboside per kg of body weight of the pig. In certain embodiments, the nicotinamide riboside is administered to the pig at a dose of at least about 5 mg, at least about 10 mg, at least about 15 mg, or at least about 30 mg of nicotinamide riboside per kg of body weight of the pig. Treatment doses providing greater amounts of nicotinamide riboside than those listed above may also be used. The dose may be administered daily for at least about 3 days, preferably at least about 5 days, and more preferably at least about 7 days. Other than the treatment doses, the pig may otherwise be given standard nursing/growing/finishing diet and water.

The methods described herein advantageously result in pigs having better average daily gain (ADG), larger loin eyes, less Longissimus lumborum (LL) surface metmyoglobin accumulation, less meat visual panelists' surface discoloration, more metmyoglobin reducing ability (MRA), and greater NAD+ content than untreated pigs. Additionally, the methods and treatments described herein increase semitendinosus muscle NAD+ levels, providing more energy for movement, and is therefore useful as a nutritional countermeasure to reduce the incidence of transport fatigue.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth studies related to the treatment of domesticated meat animals with nicotinamide riboside. It is to be understood, however, that these examples are provided by way of illustration and nothing therein should be taken as a limitation upon the overall scope of the invention.

Example 1

Objective

The objective of this study was to examine the effects of nicotinamide riboside (NR) on avian embryonic myogenesis.

Methods

At 11-days of incubation, 60 fertilized broiler eggs were randomly assigned to completely randomized design with a 2×2 factorial arrangement. Factor 1 comprised treatment, with eggs injected with 100 μl of 0.9% sterile saline solution (NRNeg) or 250 mM NR in sterile saline (NRPos). Factor 2 comprised injection location, with treatments injected into the yolk or albumen. Eggs were incubated at 37±3° C. and a relative humidity of 40±2% for 7 days. Humidity was increased to 60±2% at the same temperature for the final 3 days of incubation. Twenty-four hours after hatching, chicks were euthanized by exposure to $CO_2$ and decapitation. Measurements including chick weight and left Pectoralis major weight, length, and depth were taken for analysis.

Results

There were treatment×injection location interactions for chick weight and Pectoralis major weight and length ($P<0.02$). In all measures, there were no differences between NRNeg and NRPos chicks when treatments were injected into the albumen ($P>0.14$). However, when treatments were injected into the yolk, NRPos chicks tended to weigh more ($P=0.07$) and their Pectoralis major muscles weighed more and were longer than NRNeg chicks ($P<0.01$). There was no treatment×injection location interaction ($P=0.30$) for Pectoralis major depth. Treatment did affect ($P=0.03$) Pectoralis major depth, with NRPos chicks having thicker muscles that NRNeg chicks. (FIG. 1).

Conclusion

Injection of NR into broiler eggs at day 11 of incubation increases chick weight and improves Pectoralis major development. Injecting NR into the yolk of the developing embryo has greater positive effects on chick development when compared to injecting NR into the albumen.

Immunohistochemical Analysis

Figure 2:
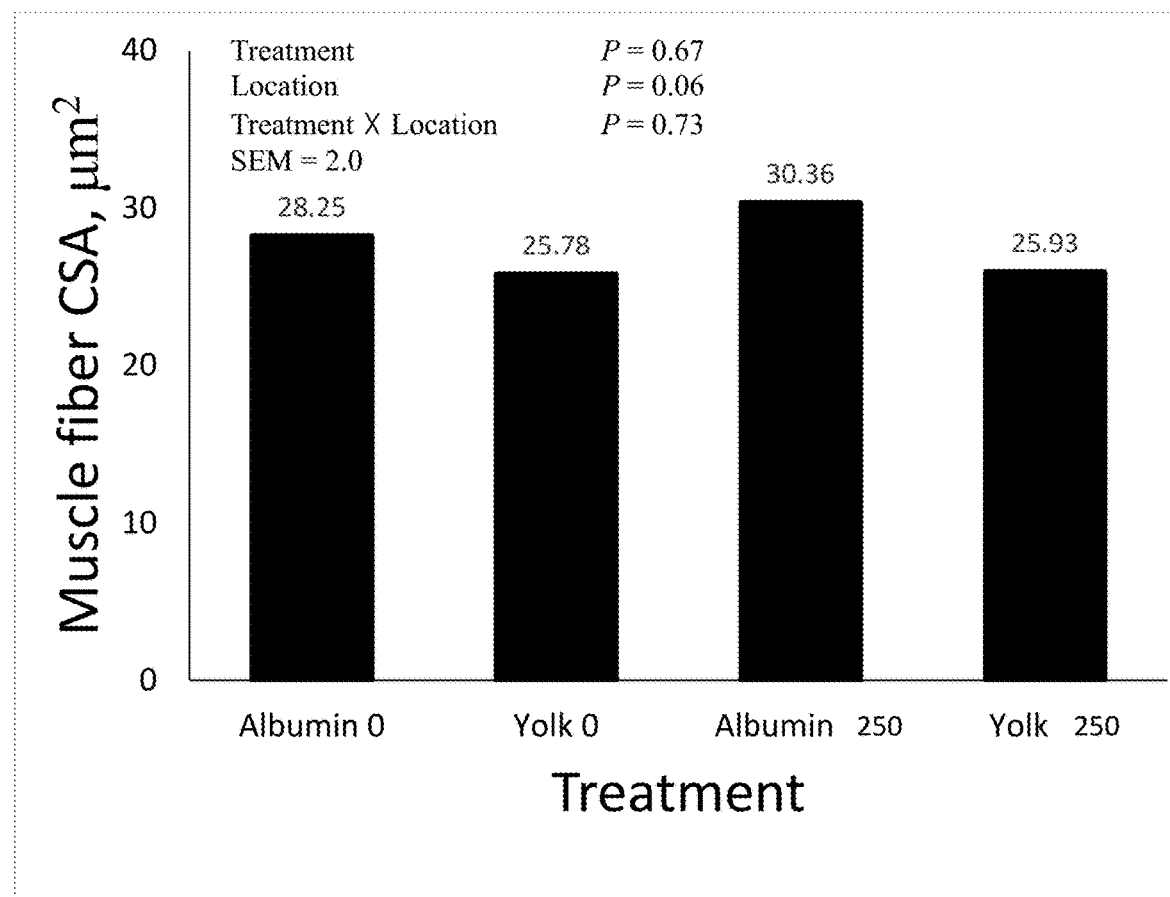
FIG. 2 is a graph showing muscle fiber cross-sectional area (CSA) during in ovo myogenesis.

Immunohistochemical analysis was conducted to determine if NR supplementation increased muscle fiber cross-sectional area (CSA) during in ovo myogenesis. There were no Treatment×Location or Treatment and Location main effects for muscle fiber CSA ($P>0.06$). See FIG. 2. Because muscle fiber CSA did not increase due to NR supplementation but whole muscle morphometrics did, it is believed that NR increased muscle morphometrics by increasing the number of muscle fibers formed during myogenesis. This is desired heavily in meat producing animals.

Example II

Objective

The objective of this study was to further examine the effect of nicotinamide riboside (NR) concentration on avian embryonic myogenesis.

Materials and Methods

Fertilized broiler eggs (n=60; Cobb 500) were randomly assigned to 1 of 4 treatments: 0.0, 250, 500, or 1,000 mM NR in sterile saline. At day 10 of incubation, 100 μl of treatment solution was injected into the egg yolk. Eggs were incubated at 37±3° C. and a relative humidity of 40±2%. At day 19 of incubation, embryos were euthanized by prolonged exposure to $CO_2$ gas and decapitation. Measurements including: embryo weight; crown-rump length; chest circumference (CC); and left Pectoralis major (PM) weight, length, width, and depth were collected.

Results

There was no treatment effect for embryo weight ($P=0.99$). Embryos treated with 1,000 mM NR had longer crown-rump measurements than all other treatments ($P<0.05$), which did not differ from each other ($P>0.36$). Embryos from the 500 and 1,000 mM treatments had larger CC and PM weight and width than 0.0 mM embryos ($P<0.04$), but did not differ ($P>0.38$) from each other. Embryos injected with 250 mM of NR did not differ in CC or PM weight and width when compared to other treatments ($P>0.06$). All NR treatments had longer PM muscles than the saline treatment ($P<0.01$), but did not differ from each other ($P<0.41$). Embryos treated with 1,000 and 250 mM NR had thicker PM muscles than saline injected embryos (P<0.04), but did not differ from each other (P=0.58). Embryos injected with 500 mM NR did not differ in PM thickness compared to other treatments (P>0.06). See Table 1.

Conclusion

Increasing the concentration of in ovo injected nicotinamide riboside has a quadratic influence on avian myogenesis. Injecting up to 500 mM NR into the yolk of the developing embryo had no effect on body weight but increased PM measures; thus, indicating NR influenced avian myogenesis.

cut into 6 chops for retail color stability analysis, including 6-day surface oxy- and metmyoglobin percentage, 6-day objective and subjective color panel evaluation, and day 4 and 6 metmyoglobin reducing ability (MRA).

Results

Figure 3:
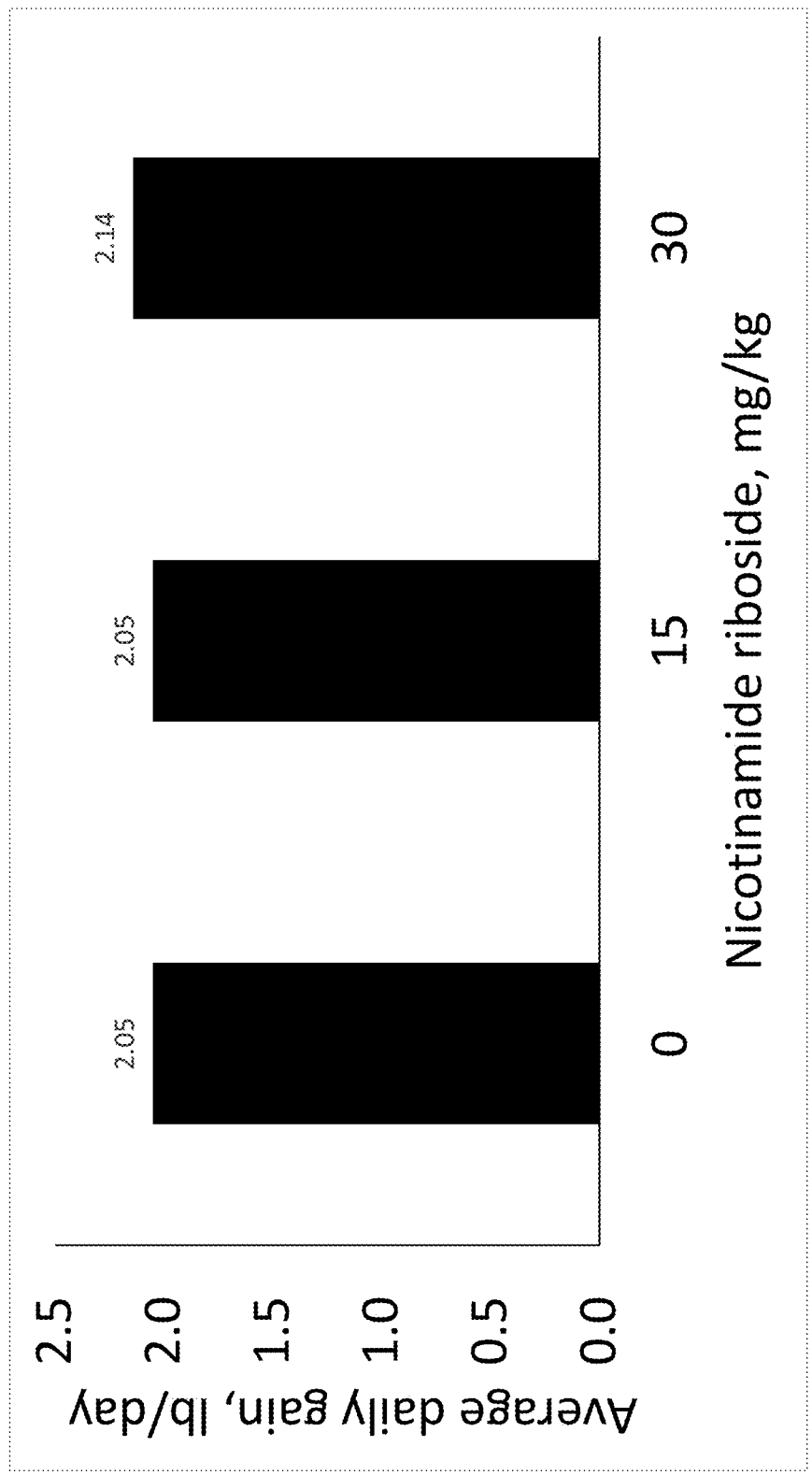
FIG. 3 is a graph showing average daily weight gain of pigs treated with nicotinamide riboside in accordance with embodiments of the present invention.

The data indicates a trend for pigs in the 30 mg/kg treatment to numerically have 4.4% better ADG when compared to pigs in the other two treatments, which did not differ (FIG. 3). Treatment tended to affect (P=0.06) LEA, with pigs fed 30 mg/kg having 52% and 48% larger loin eyes

TABLE 1

Effects of increasing nicotinamide riboside supplementation on avian in ovo myogenesis

| Item | Nicotinamide riboside dose, mM | | | | SEM | P-value |
|---|---|---|---|---|---|---|
| | 0 | 250 | 500 | 1,000 | | |
| Whole body morphometrics | | | | | | |
| Body weight, g | 46.22 | 46.42 | 46.25 | 45.97 | 1.15 | 0.99 |
| Crown to rump length, mm | 84.01$^a$ | 83.69$^a$ | 85.14$^a$ | 88.20$^b$ | 1.16 | 0.02 |
| Head width, mm | 19.51 | 15.42 | 15.49 | 15.69 | 1.87 | 0.33 |
| Head length, mm | 18.25 | 17.70 | 17.60 | 17.98 | 0.28 | 0.36 |
| Head circumference, cm | 5.3$^a$ | 5.3$^a$ | 5.6$^b$ | 5.7$^b$ | 0.1 | 0.01 |
| Chest circumference, cm | 5.3$^a$ | 6.0$^{a,b}$ | 6.3$^b$ | 6.6$^b$ | 0.3 | <0.01 |
| Pectoralis major morphometrics | | | | | | |
| Weight, g | 0.11$^a$ | 0.13$^{a,b}$ | 0.16$^b$ | 0.15$^b$ | 0.01 | 0.03 |
| Length, mm | 14.14$^a$ | 16.73$^b$ | 17.51$^b$ | 17.44$^b$ | 0.69 | <0.01 |
| Width, mm | 4.49$^a$ | 4.90$^{a,b}$ | 5.32$^b$ | 5.61$^b$ | 0.29 | 0.03 |
| Maximum thickness, mm | 2.23$^a$ | 2.56$^b$ | 2.36$^{a,b}$ | 2.64$^b$ | 0.11 | 0.04 |
| Organ weight | | | | | | |
| Heart, g | 0.23 | 0.23 | 0.23 | 0.24 | 0.01 | 0.88 |
| Liver, g | 0.69 | 0.74 | 0.72 | 0.67 | 0.04 | 0.54 |

Example III

Objective

The objective of this study was to examine the effects of nicotinamide riboside (NR) on pigs on Longissimus lumborum (LL) average daily gain (ADG), loin eye area, NAD+ content, and fresh meat color characteristics.

Methods

Figure 4:
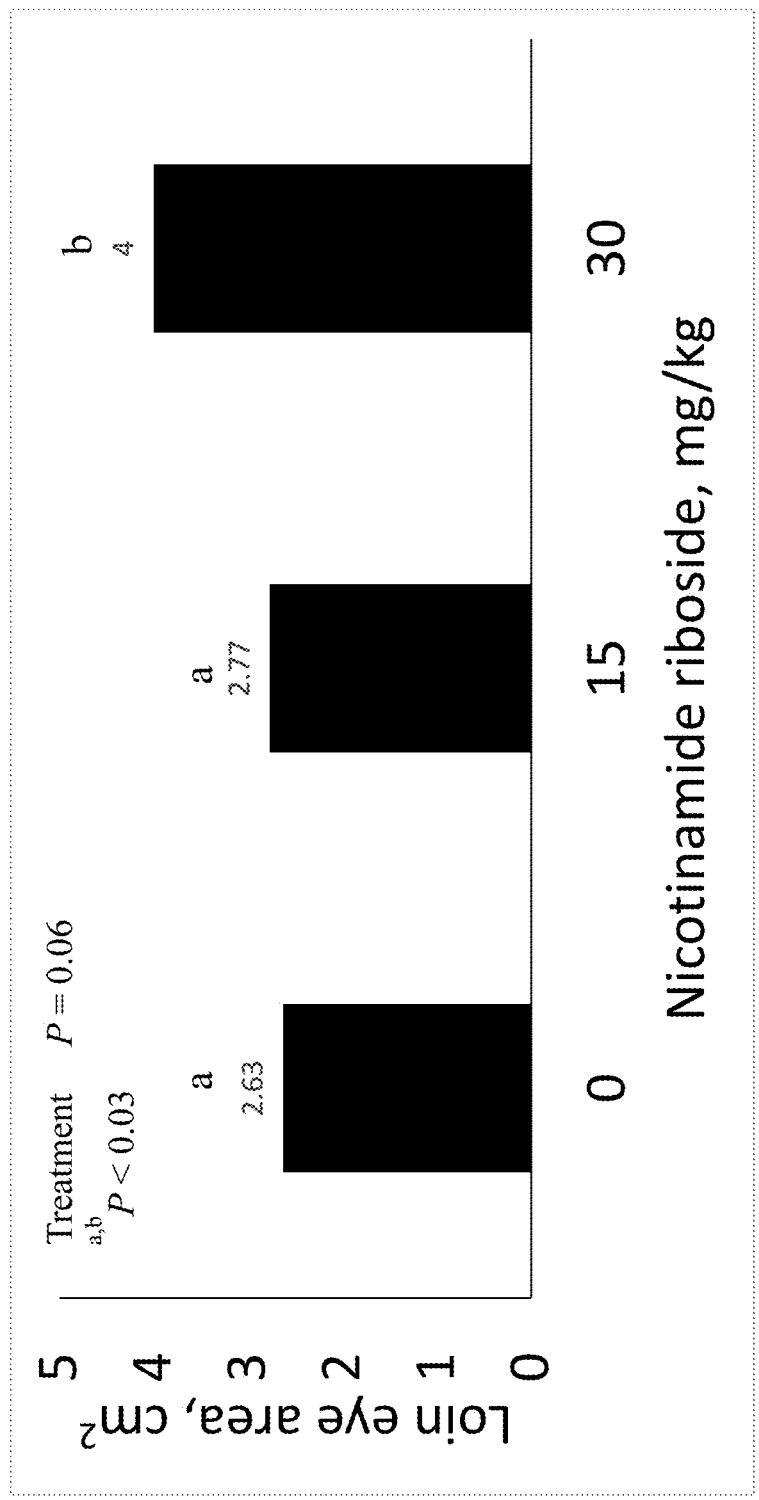
FIG. 4 is a graph showing loin eye area of pigs treated with nicotinamide riboside in accordance with embodiments of the present invention.

Nine growing pigs were blocked by bodyweight (BW) and placed in metabolism crates. After a 3-day acclimation period, pigs within each BW block were randomly assigned to a treatment (n=3 pigs/treatment). Treatments comprised pigs supplemented 0, 15, or 30 mg/kg BW NR for 7 days. Pigs were allowed ad libitum access to a standard growing diet and water. Treatments were administered daily at 8 a.m. by mixing NR in 20 mL of Karo® dark syrup and orally drenching the pigs. On day 0 and 3 of the trial, muscle biopsies of the LL were taken for NAD+ analysis using standard procedures. At day 7, pigs were transported to the Kansas State University Meats Laboratory and euthanized by a captive penetrating bolt to the brain, followed by exsanguination. Following harvest procedures, 3 g of the LL were collected for NAD+ analysis. Twenty-four hours after harvest, the whole LL not sampled at harvest was removed from the carcass and aged 10 days. After aging, the LL was than pigs fed 0 and 15 mg/kg NR, respectively (P<0.03; FIG. 4). Pigs in the 0 and 15 mg/kg treatments did not differ (P>0.15) in LEA.

Figure 5:
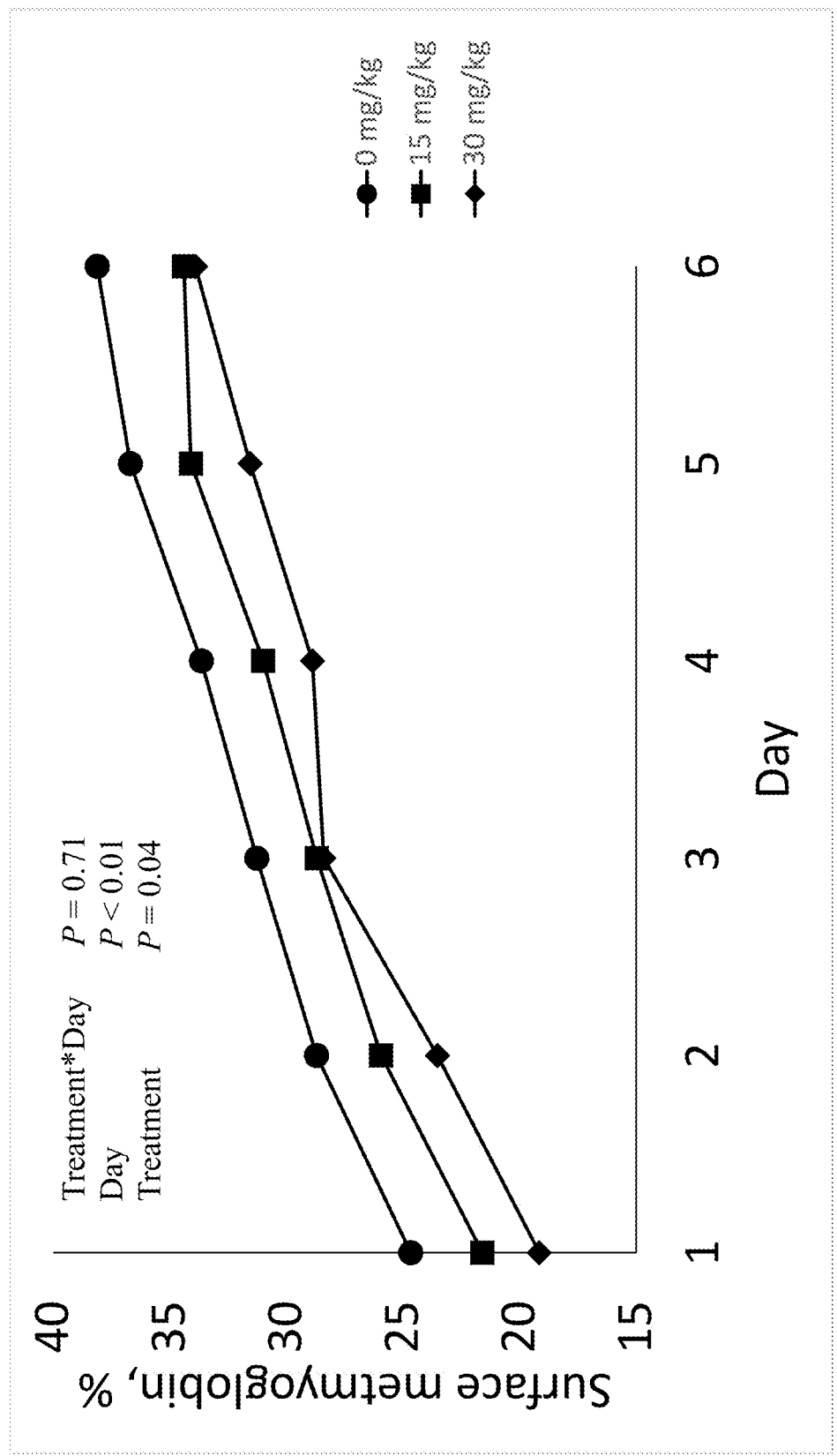
FIG. 5 is a graph showing meat surface metmyoglobin % over time of pigs treated with nicotinamide riboside in accordance with embodiments of the present invention.

There was a treatment effect (P=0.04) for surface metmyoglobin accumulation (FIG. 5). Over the entire 6-day study, LL chops from the 30 mg/kg treatment had 14% less (P=0.02) surface metmyoglobin than 0 mg/kg chops. When compared to chops from the 0 mg/kg treatment, chops from the 15 mg/kg treatment tended to have 9% less (P=0.06) surface metmyoglobin accumulation. Chops from the 15 and 30 mg/kg treatments did not differ (P=0.21) in surface metmyoglobin accumulation.

Figure 6:
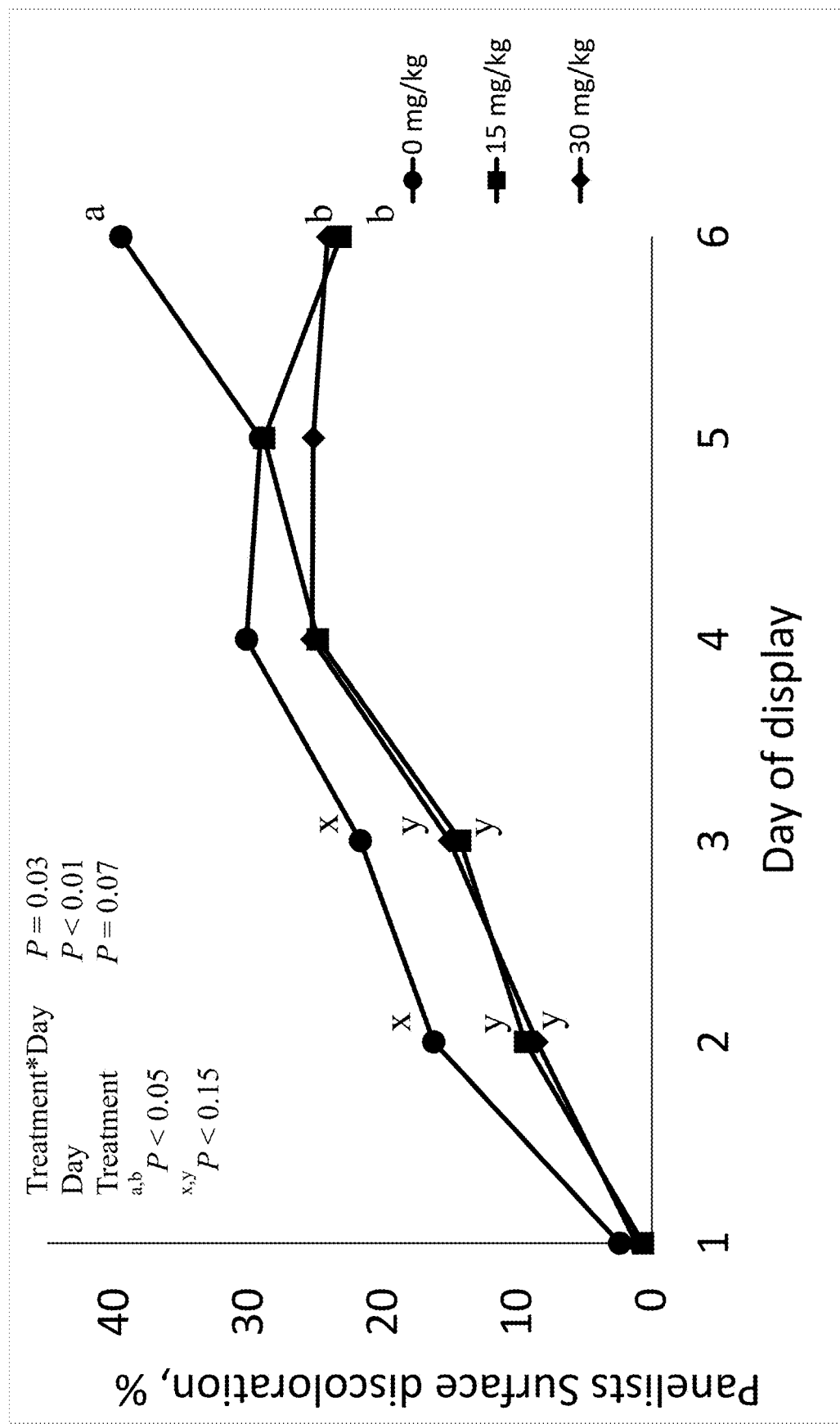
FIG. 6 is a graph showing meat panelists surface discoloration % scores over time of pigs treated with nicotinamide riboside in accordance with embodiments of the present invention.

There was a Treatment×Day interaction (P=0.03) for visual panel discoloration scores (FIG. 6). On days 1, 4, and 5 of display, treatment discoloration scores did not differ from each other (P>0.15). On days 2 and 3 of display, 0 mg/kg chops tended to have more surface discoloration than the other two treatments (P<0.12), which did not differ (P=0.83) from each other. On day 6 of display, 0 mg/kg chops had 41 and 39% greater discoloration scores than 15 and 30 mg/kg chops, respectively (P<0.01). Discoloration scores for 15 and 30 mg/kg chops did not differ (P=0.82) on this day. There was a treatment effect (P=0.04) for discoloration scores. Over the entire 6-day study, LL chops from the 30 mg/kg treatment had 30% less (P=0.04) surface discoloration than 0 mg/kg chops. When compared to chops from the 0 mg/kg treatment, chops from the 15 mg/kg treatment tended to have 27% less (P=0.06) discoloration. Chops from the 15 and 30 mg/kg treatments did not differ (P>0.15) in surface discoloration.

Figure 7:
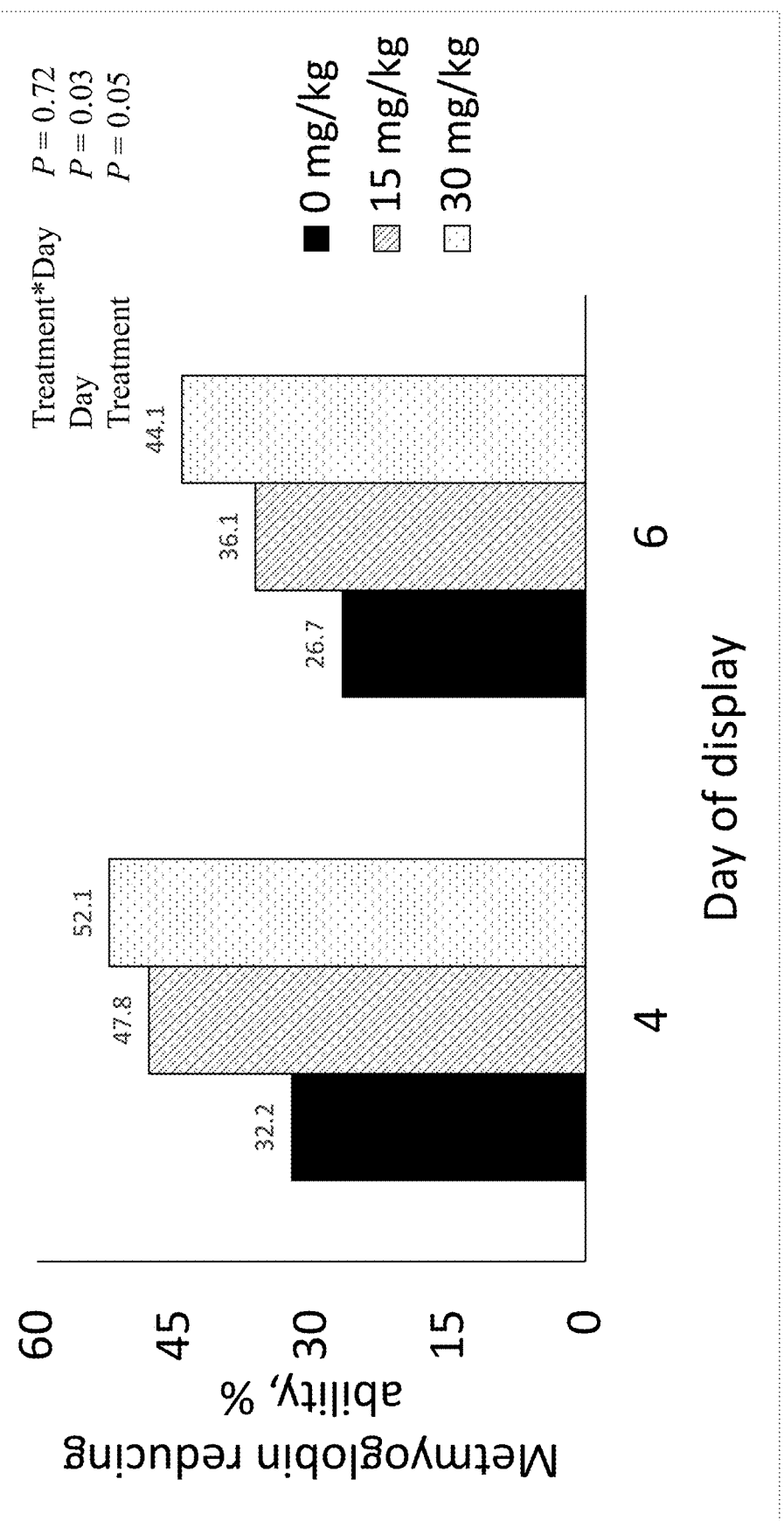
FIG. 7 is a graph showing meat metmyoglobin reducing ability % of pigs treated with nicotinamide riboside in accordance with embodiments of the present invention.
Figure 8:
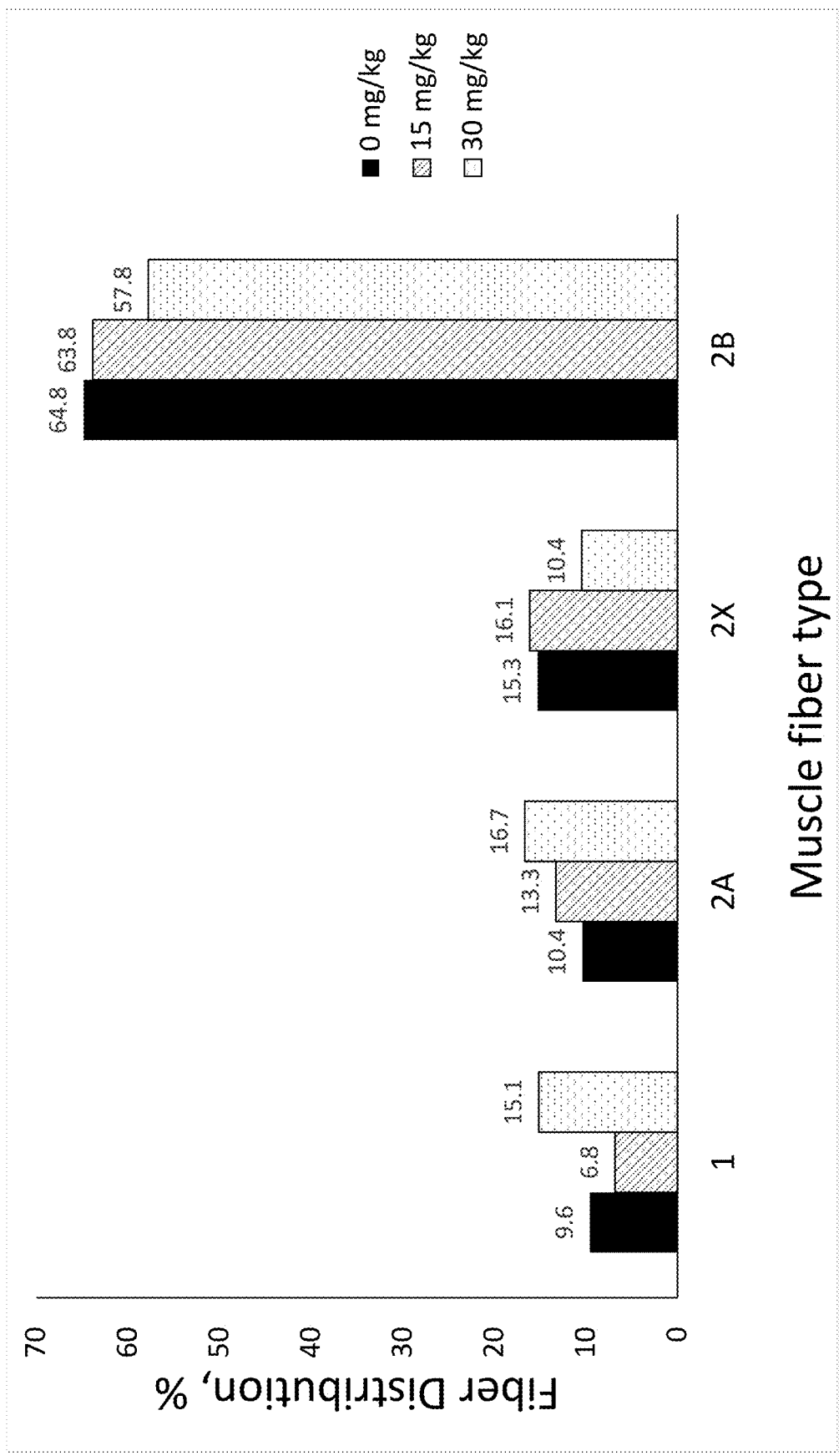
FIG. 8 is a graph showing meat muscle fiber distribution % of pigs treated with nicotinamide riboside in accordance with embodiments of the present invention.
Figure 9:
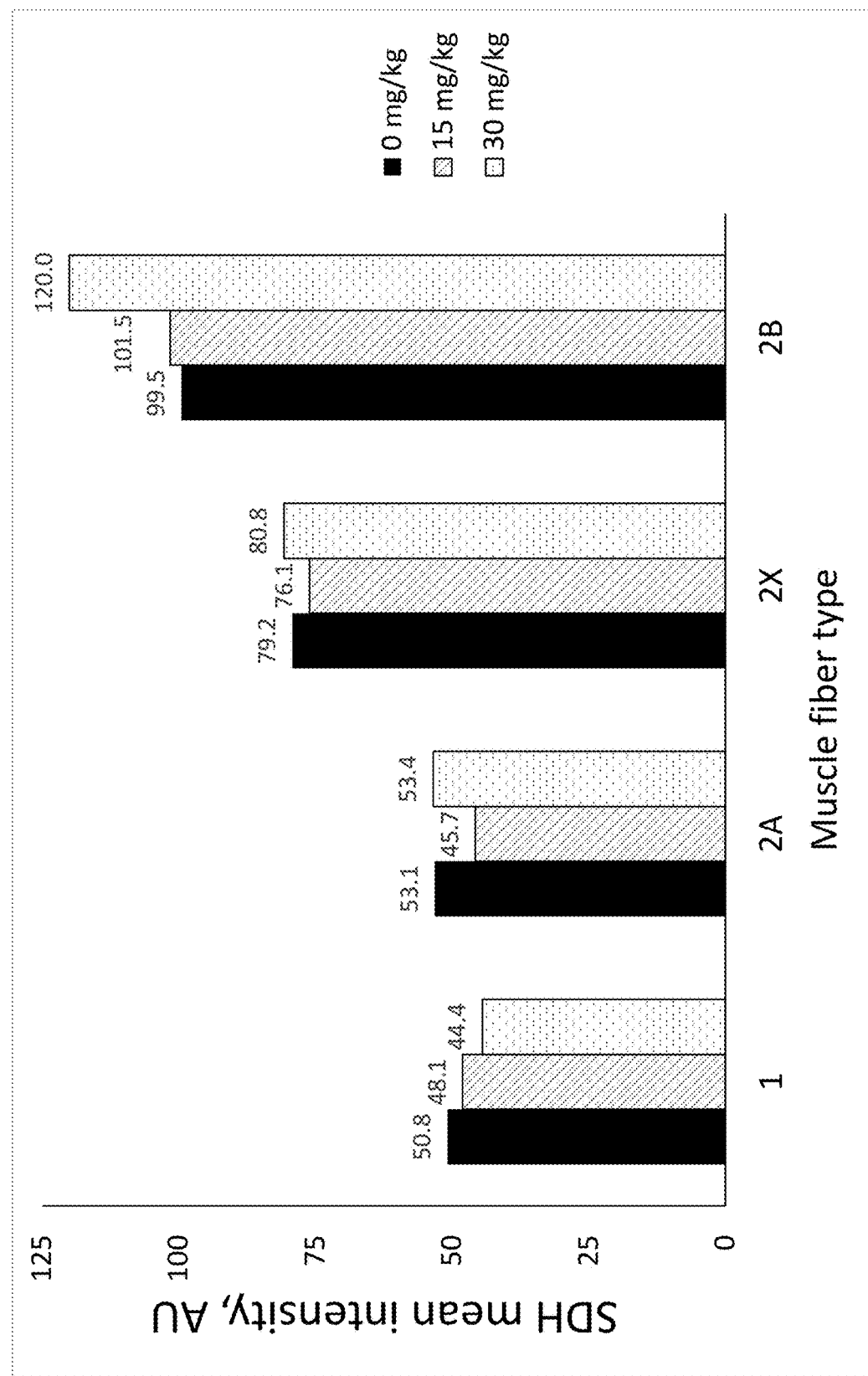
FIG. 9 is a graph showing meat muscle fiber SDH mean intensity of pigs treated with nicotinamide riboside in accordance with embodiments of the present invention.

There was a treatment effect (P=0.05) for MRA (FIG. 7). Over the entire study, LL chops from the 30 mg/kg treatment had 64% more (P=0.03) MRA than 0 mg/kg chops. When compared to chops from the 0 mg/kg treatment, chops from the 15 mg/kg treatment tended to have 42% more (P=0.08) MRA. Chops from the 15 and 30 mg/kg treatments did not differ (P=0.32) in surface discoloration. Muscle fiber distribution data indicates LL from the 30 mg/kg treatment numerically had less type 2B (glycolytic) fibers and more type 1 and 2A (oxidative) fibers than 0 mg/kg LL (FIG. 8). Succinate dehydrogenase staining indicated LL from the 30 mg/kg treatment numerically had more intense staining than LL from the other two treatments in type 2B fibers (FIG. 9).

At days 3 and 7 of NR supplementation, there were treatment effects for the total and percent LL NAD+ change (P<0.05). At days 3 and 7 of supplementation, supplementing 15 mg/kg increased NAD+ on a total and percent change basis when compared to the 0 mg/kg treatment (P=0.02). The 30 mg/kg treatment only tended to have a greater (P<0.14) total change in NAD+ content when compared to the 0 mg/kg treatment. Results of the NAD+ effects of the treatments are shown in Table 2.

Conclusion

In conclusion, supplementing NR at 30 mg/kg BW daily for 7 days appears to numerically increase ADG compared to 0 and 15 mg/kg pigs, which resulted in a tendency for LEA from these pigs to be bigger. When displayed under retail conditions, supplementing 15 or 30 mg/kg NR delayed surface accumulation of surface metmyoglobin when compared to 0 mg/kg chops, which was also seen by visual panelists. This improvement in color stability was most likely due to an improvement in MRA for both NR treatments compared to control. This improvement can partially be explained for the 30 mg/kg chops by what appears to be an increase in the number of oxidative fibers in the LL and an increase in SDH staining (oxidative ability) in type 2B fibers. Finally, supplementing NR increased NAD+ content in the LL of both NR treatments compared to control. However, the increase was greater in the 15 mg/kg treatment. It is hypothesized this may have occurred due to 30 mg/kg pigs utilizing more NAD+ for growth.

Example IV

Objective

The objective of this study was to examine the effect of oral supplementation of nicotinamide riboside (NR) on pig performance, carcass characteristics, and loin chop color stability.

Materials and Methods

Seven days prior to the beginning of the experiment, 10 finishing barrows (initial BW 111.9±1.6 kg) were assigned to individual pens located at the East Finisher facility of the Kansas State University Swine Teaching and Research Center (Manhattan, Kans.). Each pen was 7.4 m$^2$ with a slatted floor, contained a nipple waterer and an individual dry feeder that allowed ad libitum access to food and water. Barrows were randomly assigned to 1 of 2 NR treatments, 0 or 30 mg/kg daily of NR mixed in Karo® syrup and administered by oral gavage. Barrows were administered their assigned treatment for 10 days, after which they were harvested under USDA inspection. Twenty-four hours after harvest, carcass measurements were taken by trained personnel, carcasses were fabricated into the 5 major wholesale cuts, and whole-boneless loins were vacuum packaged and aged for 10 days. Loin were cut into 3 chops with chop 1 being used for day-0 metmyoglobin reducing ability (MRA) analysis, chop 2 being used for day-4 MRA and oxygen consumption rate (OCR) analyses, and chop 3 for 8-day objective/subjective color evaluation and MRA and OCR analyses.

Results

There were no treatment effects for any of the performance measures (P>0.257; Table 3). This was most likely due to the low numbers of barrows used in the pilot study. Numerically, NR supplementation increased average daily gain 8% when supplemented over 10 days.

TABLE 2

Effect of 7 days of nicotinamide riboside supplementation on pig *Longissimus lumborum* NAD+ content

| | Day 0 | | | | | | Day 7 | | | |
|---|---|---|---|---|---|---|---|---|---|---|
| Item | 0 | 15 | 30 | 0 | 15 | 30 | 0 | 15 | 30 | SEM |
| NAD+, pMol/g tissue | 8.66 | 7.70 | 8.60 | 7.75 | 9.80 | 9.31 | 9.08 | 10.42 | 9.53 | 0.77 |
| Day 3 NAD+ change | | | | | | | | | | |
| Total, pMol/g tissue | — | — | — | −0.91$^{a,x}$ | 2.10$^b$ | 0.71$^{a,b,y}$ | — | — | — | 0.66 |
| Percent change | — | — | — | −11.45$^a$ | 28.55$^{b,x}$ | 6.43$^{a,b,y}$ | — | — | — | 8.48 |
| Day 7 NAD+ change | | | | | | | | | | |
| Total, pMol/g tissue | — | — | — | — | — | — | 0.42$^{a,x}$ | 2.72$^b$ | 0.93$^{a,b,y}$ | 0.44 |
| Percent change | — | — | — | — | — | — | 5.68$^a$ | 35.29$^{b,x}$ | 10.92$^{a,b,y}$ | 5.68 |

$^{a,b}$Means lacking a common superscript within a row are different (P <0.05).

$^{x,y}$Means lacking a common superscript within a row tend to differ (P <0.15).

TABLE 3

Effect of nicotinamide riboside on finishing pig growth performance[1]

|  | Control | Nicotinamide riboside | SEM | P-Value |
|---|---|---|---|---|
| Body weight, kg | | | | |
| d 0 | 111.7 | 112.0 | 1.6 | 0.311 |
| d 7 | 116.6 | 117.0 | 1.8 | 0.855 |
| d 17 | 129.8 | 131.3 | 2.2 | 0.633 |
| d 0 to 17 | | | | |
| Average daily gain, kg | 1.1 | 1.1 | 0.1 | 0.582 |
| Average daily feed intake, kg | 3.6 | 3.8 | 0.2 | 0.531 |
| Feed to gain ratio | 3.44 | 3.42 | 0.194 | 0.929 |
| Average daily gain, kg | | | | |
| d 0 to 7 | 0.7 | 0.7 | 0.1 | 0.972 |
| d 7 to 17 | 1.32 | 1.43 | 0.06 | 0.257 |

[1]A total of 10 barrows (DNA Genetics; Columbus, NE) were individually housed in pens (n = 5). Pigs were assigned to treatments on d 7 and given an oral gavage of either 0 or 30 mg/kg NR each day from d 7 to 17.

There were no treatment effects for carcass measures and carcass fabrications measures, except for tendencies for NR to increase color score (make loin color more red) and decrease boneless loin weight (P<0.08), and NR decreased (P=0.03) Boston butt weight (Table 4). If one examines numerical trends, it appears NR increases fat deposition in all subcutaneous fat measures and marbling, but this comes at the expense of muscle deposition. This is seen with most wholesale cut weights being lower and the belly, which is mainly fat, increasing due to NR treatment.

TABLE 4

Effect of nicotinamide riboside on finishing pig carcass measures[1]

|  | Control | Nicotinamide riboside | SEM | P-Value |
|---|---|---|---|---|
| Carcass measures | | | | |
| Carcass weight, kg | 97.5 | 97.4 | 2.0 | 0.98 |
| 1st rib subcutaneous fat, cm | 1.66 | 1.76 | 0.07 | 0.33 |
| 10th rib subcutaneous fat, cm | 0.86 | 0.95 | 0.07 | 0.40 |
| Last rib subcutaneous fat, cm | 0.87 | 0.91 | 0.04 | 0.52 |
| Last lumbar subcutaneous fat, cm | 0.71 | 0.83 | 0.05 | 0.16 |
| Loin eye area, cm$^2$ | 7.78 | 7.30 | 0.23 | 0.17 |
| Color[2] | 2.6 | 3.4 | 0.3 | 0.07 |
| Marbling[3] | 1.9 | 2.4 | 0.2 | 0.24 |
| Carcass fabrication; kg | | | | |
| Boston butt | 3.78 | 3.22 | 0.15 | 0.03 |
| Picnic shoulder | 4.24 | 4.42 | 0.15 | 0.38 |
| Boneless loin | 11.58 | 10.39 | 0.43 | 0.08 |
| Belly | 7.42 | 7.93 | 0.35 | 0.33 |
| Ham | 10.31 | 9.63 | 0.28 | 0.12 |

[1]A total of 10 barrows (DNA Genetics; Columbus, NE) were individually housed in pens (n = 5). Pigs were assigned to treatments on d 7 and given an oral gavage of either 0 or 30 mg/kg NR each day from d 7 to 17.
[2]National Pork Producers Council color scores:
1 = pale pinkish gray to white;
2 = grayish pink;
3 = reddish pink;
4 = dark reddish pink;
5 = purplish red;
6 = dark purplish red.
[3]National Pork Producers Council marbling scores: 1 = none and 10 = abundant.

There were no Treatment×Day interactions for all objective and subjective color measurements (P>0.77). Day of display affected all measures consistent with the discoloration of meat (P<0.02), except L* (lightness; 0=black and 100=white) value which was not affected (P=0.14; Table 5).

Figure 10:
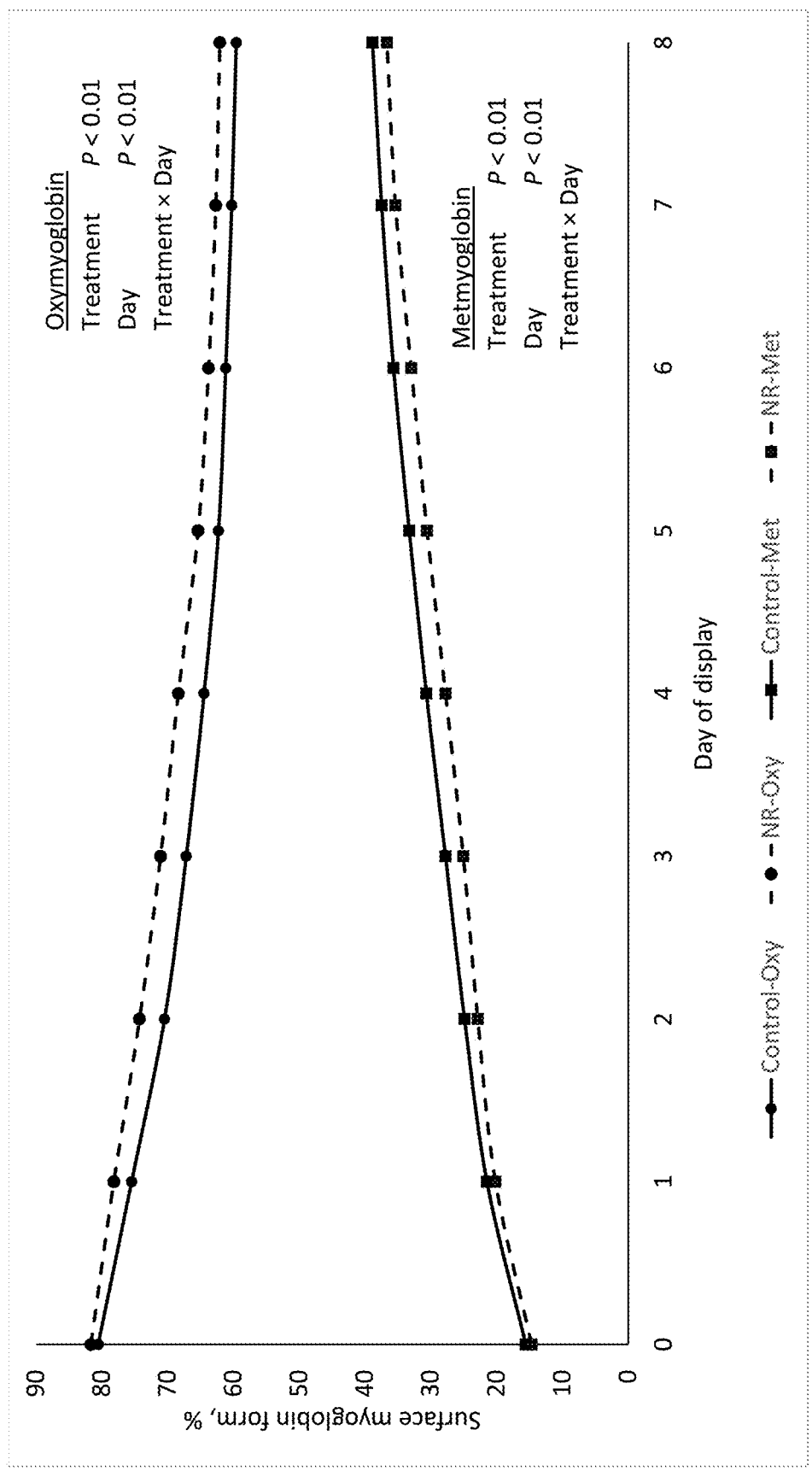
FIG. 10 is a graph showing Objective loin chop surface oxy- and metmyoglobin accumulation from pigs fed 0 or 30 mg/kg of nicotinamide riboside (NR) for the final 10 days of feeding.
Figure 11:
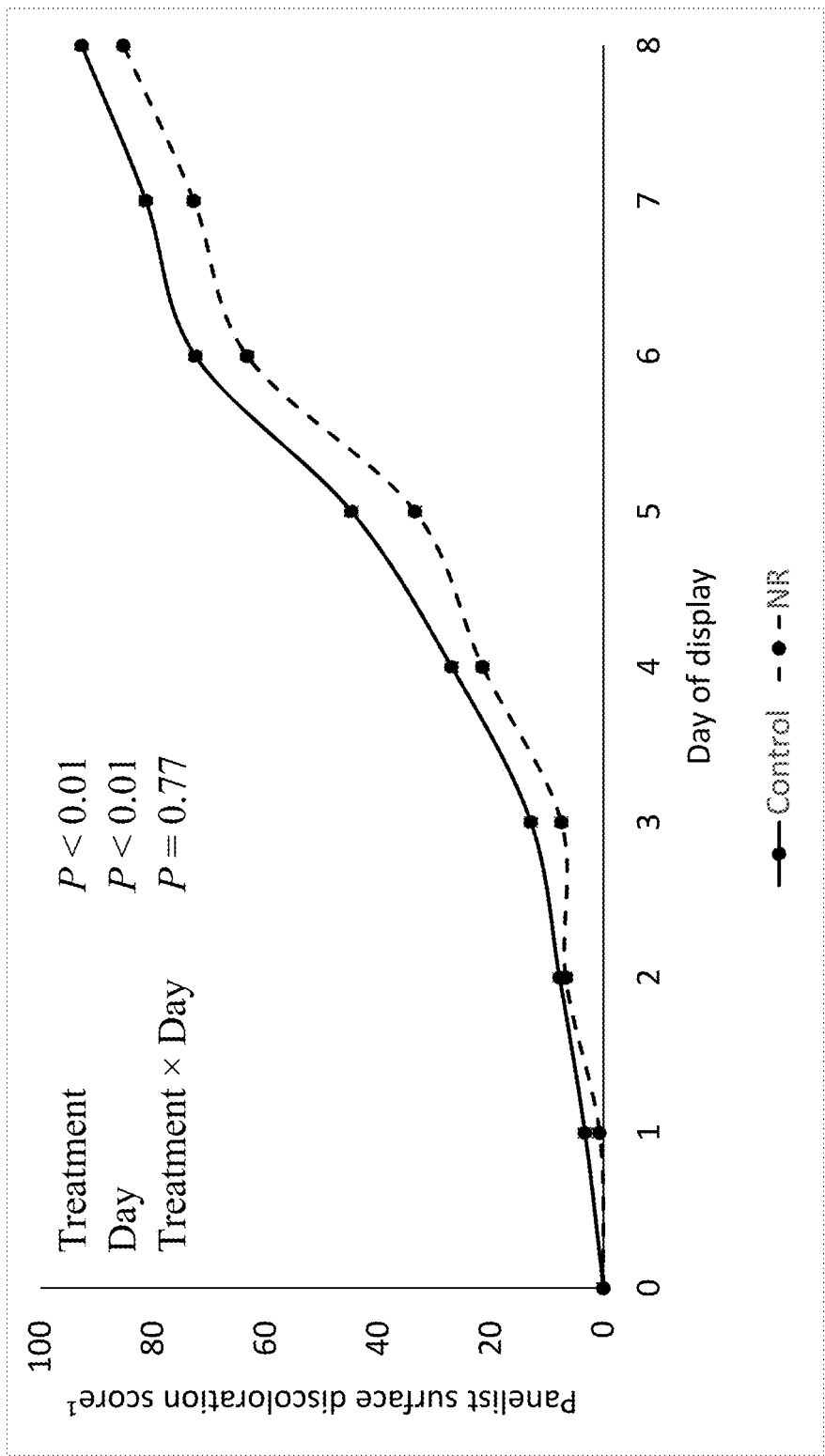
FIG. 11 is a graph showing trained panelists loin chop discoloration scores from pigs fed 0 or 30 mg/kg of nicotinamide riboside (NR) for the final 10 days of feeding.
Figure 12:
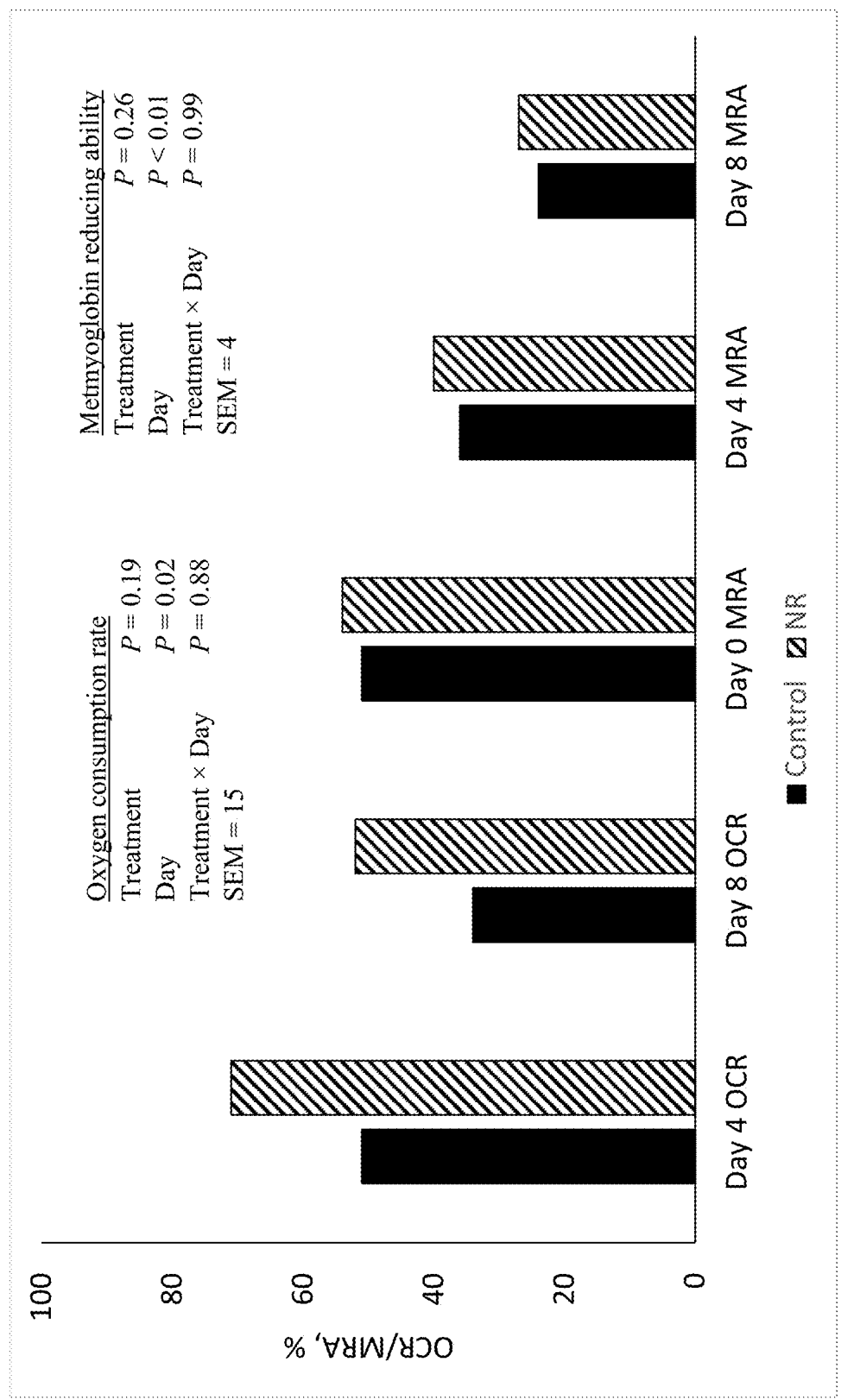
FIG. 12 is a graph showing oxygen consumption rate and metmyoglobin reducing ability of pigs fed 0 or 30 mg/kg of nicotinamide riboside (NR) for the final 10 days of feeding.

FIG. 10 shows objective loin chop surface oxy- and metmyoglobin accumulation from pigs fed 0 or 30 mg/kg of nicotinamide riboside (NR) for the final 10 days of feeding. Chops were displayed under simulated retail display for 8 days and percent of surface oxymyoglobin and metmyoglobin were calculated using the equations of Krzywicki (1979). Objective measures indicated NR chops had greater a* (redness; −60=green and 60=red), greater surface oxymyoglobin, and less surface metmyoglobin formation over the 8-day display period (P<0.01; Table 5 and FIG. 10). FIG. 11 shows trained panelists loin chop discoloration scores from pigs fed 0 or 30 mg/kg of nicotinamide riboside (NR) for the final 10 days of feeding. Chops were displayed under simulated retail display for 8 days and 8 to 10 panelists evaluated discoloration on line scales with the following anchors: 0=0% discoloration and 100=100% discoloration. Panelists indicated chops had less discoloration form over the entire 8-day display period (P<0.01; FIG. 11). FIG. 12 shows oxygen consumption rate and metmyoglobin reducing ability of pigs fed 0 or 30 mg/kg of nicotinamide riboside (NR) for the final 10 days of feeding. Chops were displayed under simulated retail display for 8 days and OCR and MRA were calculated as outlined in the American Meat Science Association's (AMSA) Meat Color Measurement Guidelines (AMSA, 2012). While treatment did not affect OCR and MRA (P>0.19), NR chops did have greater OCR and MRA during the 8-day display study.

TABLE 5

Effect of nicotinamide riboside on loin chop L* and a* values[1]

|  | Control | Nicotinamide riboside | SEM | Treatment | Day | Treatment × Day |
|---|---|---|---|---|---|---|
| L*[2] | | | 1.0 | 0.76 | 0.14 | 1.00 |
| 0 | 64.8 | 64.4 | | | | |
| 1 | 65.0 | 65.2 | | | | |
| 2 | 63.5 | 63.7 | | | | |
| 3 | 63.7 | 63.4 | | | | |
| 4 | 62.6 | 63.1 | | | | |
| 5 | 62.6 | 62.9 | | | | |
| 6 | 62.8 | 62.7 | | | | |
| 7 | 62.2 | 62.8 | | | | |
| 8 | 62.5 | 62.8 | | | | |
| a*[3] | | | 0.4 | <0.01 | <0.01 | 1.00 |
| 0 | 19.3 | 19.7 | | | | |
| 1 | 18.4 | 18.8 | | | | |
| 2 | 17.8 | 18.6 | | | | |
| 3 | 16.8 | 17.8 | | | | |
| 4 | 16.3 | 17.3 | | | | |
| 5 | 15.3 | 16.3 | | | | |
| 6 | 14.7 | 15.6 | | | | |
| 7 | 14.3 | 15.1 | | | | |
| 8 | 13.9 | 14.7 | | | | |

[1]A total of 10 barrows (DNA Genetics; Columbus, NE) were individually housed in pens (n = 5). Pigs were assigned to treatments on d 7 and given an oral gavage of either 0 or 30 mg/kg NR each day from d 7 to 17.
[2]0 = black and 100 = white.
[3]−60 = green and 60 = red.

Conclusion

Feeding NR the final 10 days before harvest numerically improved ADG and carcass fat measures at the expense muscle deposition. Loin chops from NR pigs were redder and had better color stability than control chops. Feeding NR at the end of the finishing period can be a useful way to increase carcass fatness (most importantly belly weight) and increase the time pork can be sold at retail.

Example V

Objective

A study was conducted to determine the effects of nicotinamide riboside (NR) on finished market barrow fatigue and semitendinosus muscle nicotinamide adenine dinucleotide (NAD+) content.

Methods

Fourteen days prior to harvest, 20 finished market barrows (initial body weight 268 pounds) were randomly assigned to 1 of 2 treatments: 0 or 30 mg/kg body weight of nicotinamide riboside, both orally administered daily in 20 ml of Karo® Syrup. Ten days prior to harvest, pigs were restrained via a snare and treatments were administered. On day 7, barrows were subjected to a performance test where they were walked around a track at 0.88 m/s until subjective fatigue was achieved. Three days following the performance test, barrows were harvested and a portion of the semitendinosus muscle was collected within 45 minutes. These samples were analyzed for NAD+ content via HPLC methodology.

Results

Figure 13:
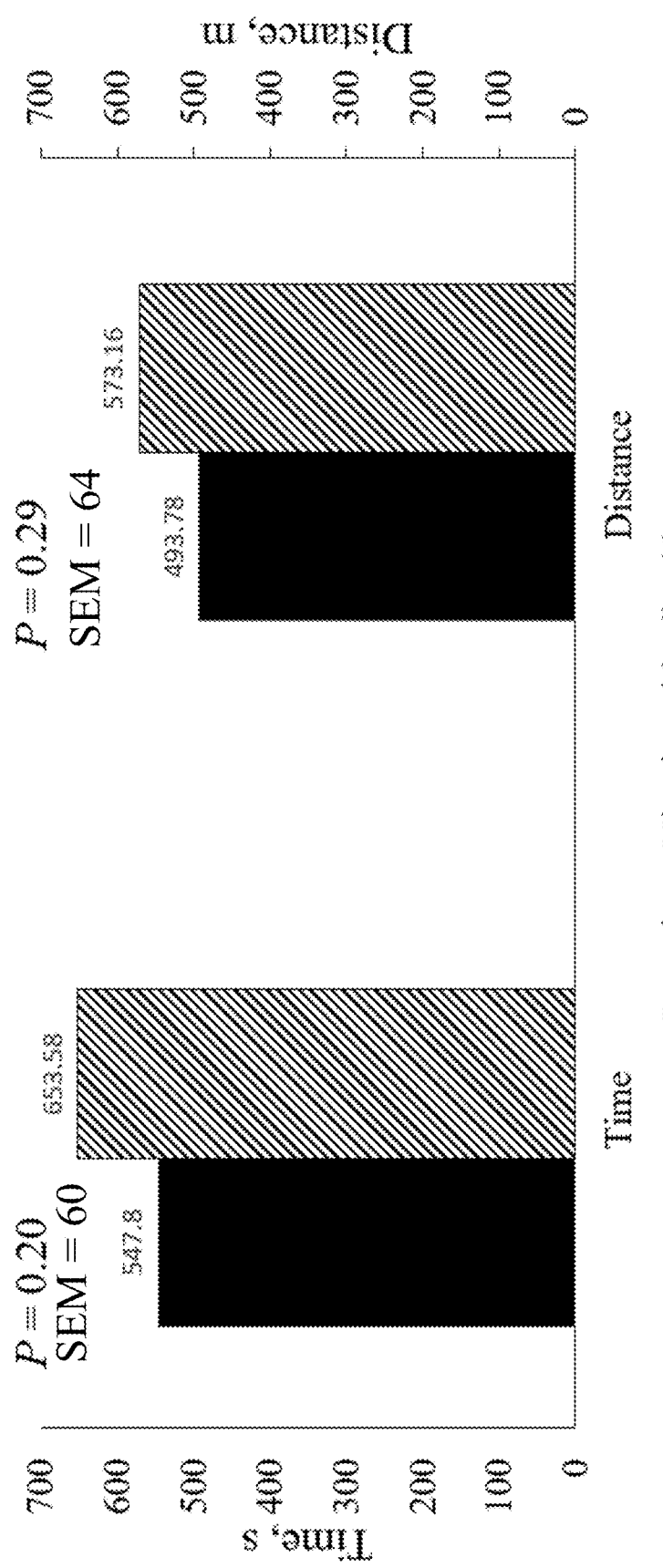
FIG. 13 is a graph showing the effect of nicotinamide riboside on the onset of subjective fatigue.
Figure 14:
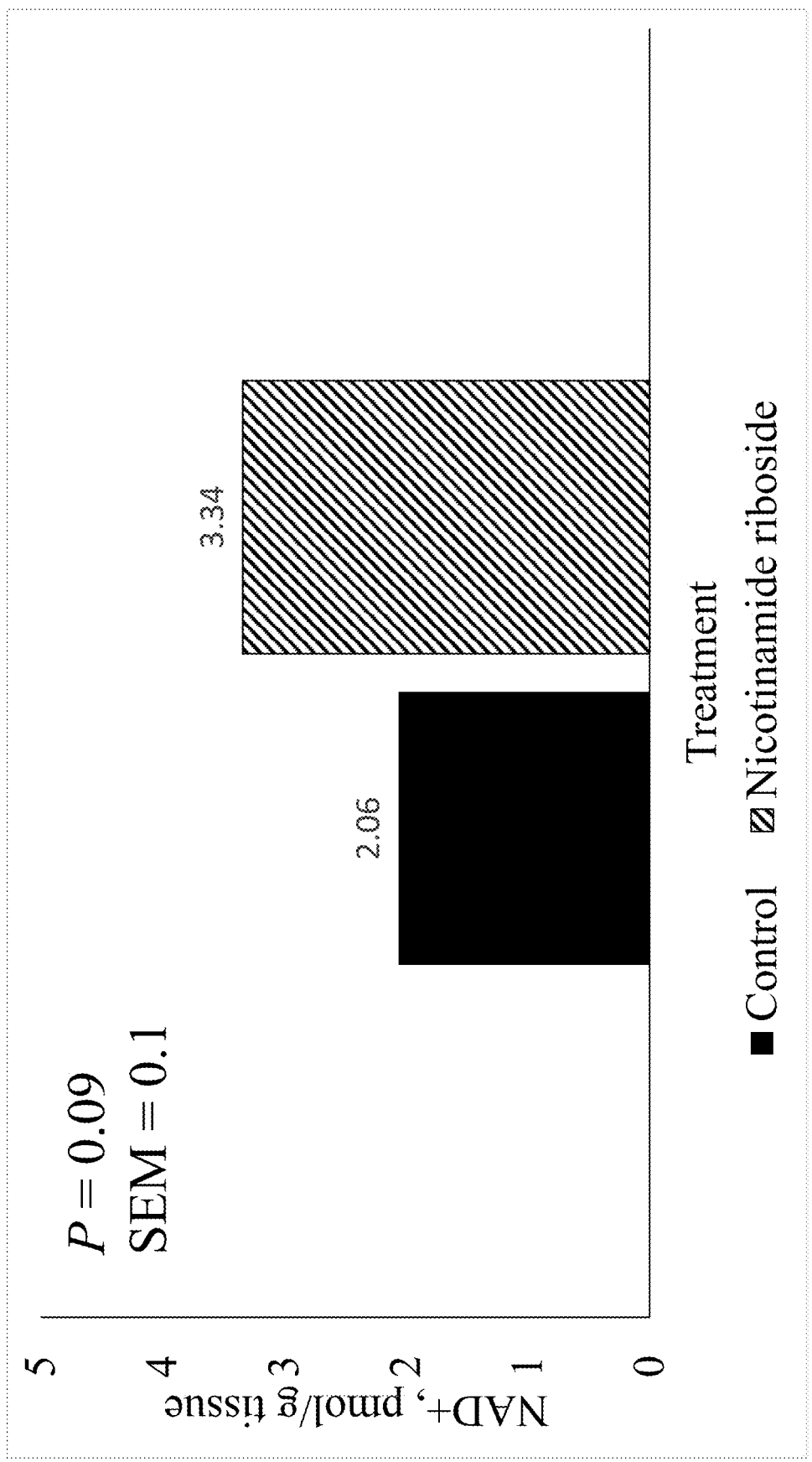
FIG. 14 is a graph showing the effect of nicotinamide riboside on Semitendinosus nicotinamide adenine dinucleotide (NAD+) concentration.

Data indicated NR supplemented barrows numerically ran longer and farther by 19 and 16%, respectively (FIG. 13). There was a tendency (P=0.09) for NR supplementation to increase the amount of NAD+ in the semitendinosus muscle by 62% (FIG. 14).

Discussion

No previous study has been conducted that examined the ability of nicotinamide riboside chloride to delay the onset of fatigue in pigs. This study demonstrated that feeding 30 mg/kg body weight of nicotinamide riboside to finished market barrows (280-300 pounds) numerically increased the time and distance barrows moved when they were subjected to a performance test. The study also demonstrated barrows fed 30 mg/kg body weight of nicotinamide riboside had greater semitendinosus muscle nicotinamide adenine dinucleotide (NAD+) content. Therefore, these data indicate supplementing nicotinamide riboside to finished market barrows delays the onset of fatigue, possibly by increasing muscle NAD+ content, and may serve as a countermeasure to prevent transportation losses.

Conclusion

Feeding 30 mg/kg body weight of nicotinamide riboside 7 days prior to a performance test increased the time and distance barrows moved. Nicotinamide riboside also increased semitendinosus muscle NAD+ levels, which could provide more energy for movement. This product may have potential to serve as a nutritional countermeasure to reduce the incidence of transport fatigue.

Example VI

Objective

The objective of this study was to examine the effects of NR in ovo feeding on broiler pectoralis major growth and development.

Materials and Methods

Egg Procurement, Incubation, and Injections

Fertilized broiler eggs (N=156; Cobb 500; Cobb-Vantress, Siloam Springs, Ark.) with an average weight of 70.3 g were transported in coolers to the Kansas State University Muscle Biology Laboratory (Manhattan, Kans.). Upon arrival, egg weights were recorded, eggs were ordered by weight, and within each 4 egg strata, eggs were randomly assigned to treatments within a 2×2 factorial arrangement. Factor 1 was NR treatment with eggs receiving 0 or 250 mM NR (ChromaDex, Los Angeles, Calif.). Factor 2 was injection location, with treatments injected into either the yolk or albumen. After treatment assignment, eggs were positioned with equal treatment representation onto trays and placed in an incubator (Sportsman 1502; GQF Manufacturing Company Inc., Savannah, Ga.) set to operate at a temperature of 37° C. and a relative humidity of 40±2% for the first 18 d of incubation. The incubator rotated hourly to reposition eggs, and trays were rotated daily throughout the incubator to account for variation in temperature and humidity. Tray weights were recorded each day to determine egg weight loss percentage with a target weight loss of 0.67% per day.

Injection Procedure

At d 10 of incubation, NR with the equivalent weight of 250 mM was added to 0.9% sterile saline and covered with foil to prevent exposure to light. Sets of 20 eggs representing equal treatment numbers were removed from the incubator, candled to determine location of the yolk and albumen, and the injection site was cleaned with 70% ethanol. Eggs were turned at a 90° angle and a 2.54-cm, 20-guage hypodermic needle was used to create an opening in the shell at the proper injection site. The needle was inserted approximately 1 cm into injection site and 100 µl of the 250 mM NR solution or 0.9% saline solution was injected into the egg. A 1-$cm^2$ portion of medical tape (Nexcare; 3M, Maplewood, Minn.) was positioned over the injection location and eggs were returned to the incubator.

Hatching, Euthanasia, and Processing

On d 18 of incubation, the relative humidity of the incubator was increased to 60±2% and eggs were placed into hatching boxes at the bottom of the incubator. As chicks began to hatch, they were removed from the incubator, marked for treatment, and relocated to a box positioned underneath a heat lamp. Approximately 12 to 24 h after hatch, chicks were euthanized by prolonged exposure to $CO_2$ gas and decapitation. Chick weights were recorded, and digital calipers (Traceable Digital Calipers; Fisher Scientific, Pittsburg, Pa.) were utilized to measure crown to rump length, head width, head length. Head and chest circumference were also collected by wrapping a string around the designated area and determining the length against a ruler.

Chick carcasses were sprayed with 70% ethanol and the skin and feathers were pulled back to reveal the pectoralis major (PM) muscles. Prior to PM muscles removal, chest width and length were measured using digital calipers. The left and right PM muscles were removed, careful to not remove the pectoralis minor muscles. The left PM was weighed and dimensions were collected using digital calipers, including length, width, and depth. This muscle was positioned onto a tongue depressor and placed into a −80° C. freezer, where it was stored until it was used for cryosectioning. The heart and liver were also removed, weighed, and discarded.

Immunohistochemistry

The methods of Noel et al. (2016) were followed for immunohistochemistry with modifications. The PM was removed from the tongue depressor, embedded in tissue embedding media (Fisher Scientific), cooled with isopentane chilled liquid nitrogen, and stored at −80° C. until cryosectioning. Ten micrometer-thick cryosections were cut using a Microm 550 cryostat (Thermo Fisher Scientific, Kalamazoo, Mich.) and six cryosection were collected on positively charged slides (Diamond White Glass; Globe Scientific Inc., Paramus, N.J.). Cryosections were incubated in a blocking solution containing 5% horse serum and 0.2% TritonX-100 in Phosphate Buffered Saline (PBS) for 30 min. Slides were incubated for 1 h at room temperature in a primary antibody solution consisting of blocking solution and 1:500 rabbit, α-dystrophin (Thermo Fisher Scientific). Cryosections were washed 3 times for 5 min each in PBS and incubated for an additional 30 min with blocking solution containing 1:1,000 Alexa-Flour 594 goat-anti-rabbit heavy and light chains (Life Technologies, Carlsbad, Calif.). Cryosections were washed again as stated above, 5 µl of 9:1 glycerol in PBS was placed on each section, and slides were coverslipped for imaging. Cryosections were visualized at 200× magnification using a Nikon Elipse TI-U inverted microscope (Nikon Instruments Inc., Melville, N.Y.), a Nikon DS-QiMC digital camera (Nikon Instruments Inc.) was used to photograph cryosections, and an average of 1,000 fibers were analyzed using NIS-Elements imaging software (Basic Research, 3.3; Nikon Instruments Inc.) to determine fiber cross-section area (CSA).

Statistics

Data were analyzed as a completely randomized design with a 2×2 factorial arrangement and egg as the experimental unit. Nicotinamide riboside treatment (TRT) and injection location (LOC) served as fixed effects. The PROC MIXED procedure of SAS 9.4 (SAS Inst. Inc., Cary, N.C.) was utilized and pairwise comparisons between the least square means were computed using the PDIFF option of the LSMEANS statement. Differences were considered statistically significant at $P<0.05$.

Results

There were no TRT×LOC interactions for all measures ($P>0.07$; Table 6), except PM weight and length ($P<0.01$). Pectoralis major weights of chicks injected with NR in the albumen were not different ($P=0.09$) when compared to chicks injected with saline in the albumen; however, chicks injected with NR in the yolk had greater ($P<0.01$) PM weights than those injected with saline. Pectoralis major lengths of chicks injected with NR in the albumen were longer ($P=0.04$) than those injected with saline. Lengths of chicks injected with NR in the yolk were longer ($P<0.01$) than those injected with saline, but the difference was greater than the albumen response.

TABLE 6

Body and pectoralis major morphometrics of hatched chicks injected in ovo with nicotinamide riboside during embryogenesis

| Nicotinamide riboside dose[1] | 0 mM | | 250 mM | | | P-value[2] | | |
|---|---|---|---|---|---|---|---|---|
| Injection location[3] | Albumen | Yolk | Albumen | Yolk | SEM | TRT | LOC | TRT × LOC |
| Body measurements | | | | | | | | |
| Weight, g | 42.69 | 42.99 | 43.19 | 44.02 | 6.40 | 0.17 | 0.31 | 0.63 |
| Dimensions, mm length | | | | | | | | |
| Crown-rump | 95.60 | 96.93 | 96.14 | 89.36 | 3.70 | 0.12 | 0.23 | 0.07 |
| Head width | 15.40 | 15.74 | 15.56 | 15.45 | 0.40 | 0.67 | 0.48 | 0.21 |
| Head length | 21.79 | 21.86 | 21.29 | 21.73 | 0.19 | 0.42 | 0.51 | 0.63 |
| Head circumference | 32.38 | 32.08 | 32.14 | 31.49 | 1.60 | 0.70 | 0.66 | 0.87 |
| Chest length | 22.01 | 21.96 | 21.98 | 22.68 | 0.55 | 0.36 | 0.39 | 0.29 |
| Chest width | 16.90 | 17.35 | 16.57 | 17.69 | 0.33 | 0.98 | 0.01 | 0.28 |
| Heart weight, g | 0.36 | 0.36 | 0.35 | 0.36 | 0.02 | 0.75 | 0.55 | 0.24 |
| Liver weight, g | 1.09 | 1.08 | 1.05 | 1.11 | 0.06 | 0.64 | 0.36 | 0.19 |
| Pectoralis major measurements | | | | | | | | |
| Weight, g | 0.13$^a$ | 0.13$^a$ | 0.14$^a$ | 0.18$^b$ | 0.01 | <0.01 | <0.01 | <0.01 |
| Dimensions, mm | | | | | | | | |
| Length | 17.55$^a$ | 17.04$^a$ | 18.68$^b$ | 20.74$^c$ | 0.43 | <0.01 | 0.06 | <0.01 |
| Width | 4.59 | 4.62 | 4.81 | 5.21 | 0.22 | <0.01 | 0.13 | 0.20 |
| Depth | 2.27 | 2.32 | 2.43 | 2.65 | 0.09 | <0.01 | 0.09 | 0.30 |

$^{abc}$Treatments with different superscripts within a row differ (P <0.05).
[1]100 µl of 0.9% saline containing 0 or 250 mM nicotinamide riboside injected at d 10 of incubation.
[2]TRT denotes nicotinamide riboside treatment main effect; LOC denotes injection location main effect.
[3]Treatments were injected into either the yolk sac or albumen of the egg.

Treatment did not affect whole body or organ measures ($P>0.12$); however, NR treatment did increase PM weight, length, width, and depth ($P<0.01$). There were no LOC main effects for all measures ($P>0.06$), with the exception of an increased chest width and PM weight when injection took place in the yolk ($P=0.01$).

Figure 15:
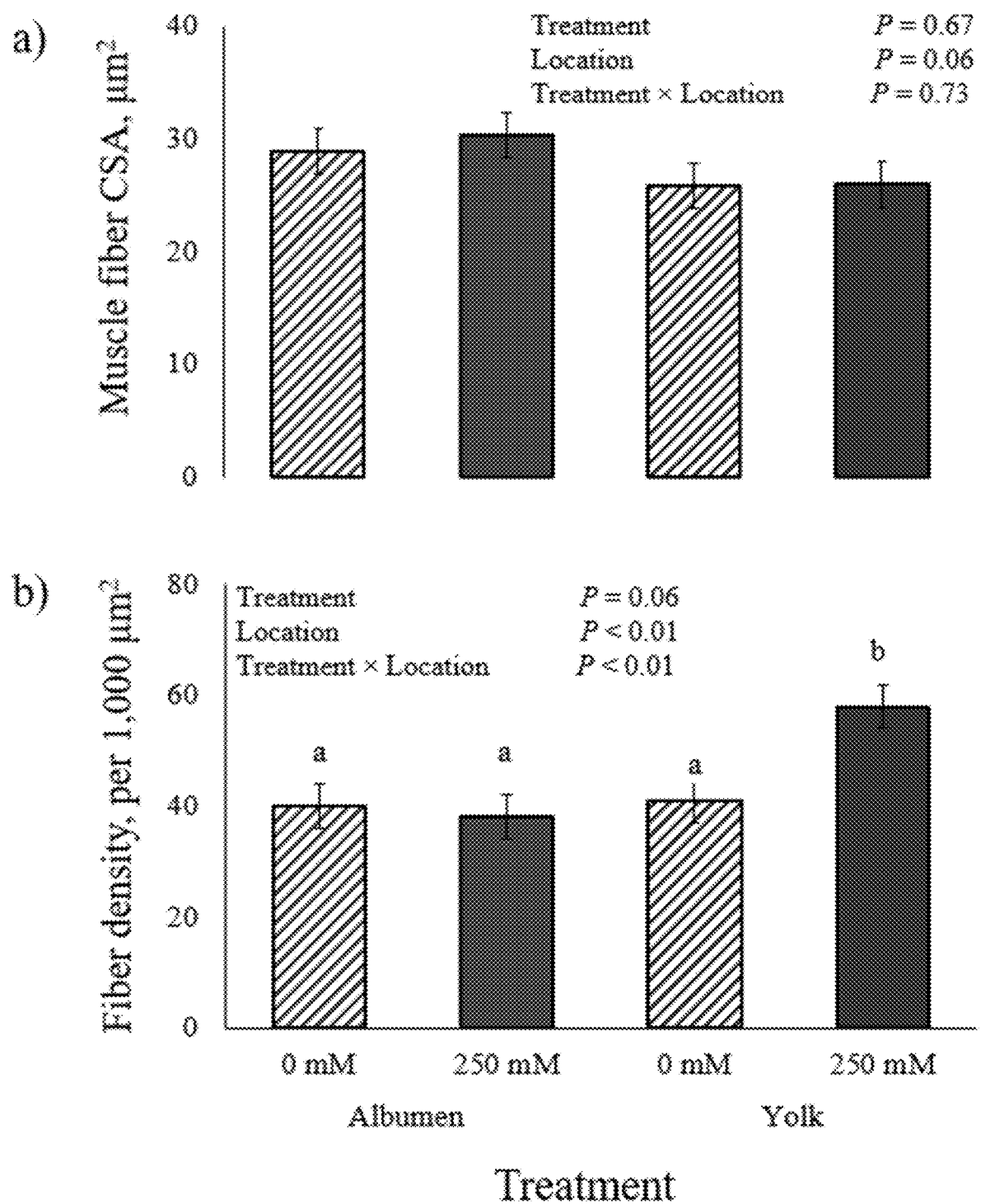
FIG. 15 is a graph showing pectoralis major a) Muscle fiber cross-sectional area (CSA) and b) density of hatched chicks fed in ovo with nicotinamide riboside (NR) during embryogenesis ($^{a,b}$Means with different superscripts differ (P<0.05)

There were no TRT×LOC interaction or LOC and TRT main effects for muscle fiber CSA ($P>0.06$; FIG. 15). There was a TRT×LOC interaction for muscle fiber density ($P<0.01$). Chicks injected with NR in the albumen were not differ ($P=0.09$) in fiber density when compared to chicks injected with saline in the albumen; however, chicks injected with NR in the yolk had more ($P<0.01$) muscle fibers than those injected with saline. The TRT main effect did not affect ($P=0.06$) muscle fiber density, but chicks injected in the yolk had more ($P<0.01$) fibers than chicks injected in the albumen.

Discussion

In ovo feeding is the practice of injecting compounds into various locations within the incubating egg. While the literature does not indicate why the industry has not widely adopted this practice, the fact that some compounds are toxic or subject to extra regulations may provide an explanation for lack of adoption. Therefore, identifying compounds that improve muscle development but are considered natural can be beneficial to the industry.

Of the major protein producing industries, the broiler industry has made the greatest advancement in production efficiency and yield. Over a 25-year period ending in 2010, broiler market weight increased almost 75% on only 0.44 kg more feed. Genetic selection and advancements in nutrient utilization are factors responsible for improved production efficiency. Aside from efficiency of nutrient utilization, the most notable improvement in broiler production is the amount of deposited carcass muscle. In the current study, in ovo feeding of NR did not affect any whole-body morphometric measurements or heart and liver weight. While whole-body measures were unaffected by NR injection, administration of NR into the yolk sac increased PM weight and length by 38 and 22%, respectively. Regardless of injection location, NR also increased PM width and depth by 9 and 11%, respectively.

The two major events of broiler embryo muscle development include primary muscle fiber formation, followed by secondary muscle fiber formation. Primary myogenesis in the avian embryo encompasses d 3 to 7 of incubation, while secondary myogenesis occurs from d 8 until hatch. In the current study, in ovo feeding occurred at d 10 of incubation which is well into the events of secondary myogenesis. Feeding NR at this time period did not affect PM fiber CSA, but injecting NR into the yolk sac increased PM fiber density by 45%. The NR response documented in the current study elicited the greatest increase in PM fiber density of known in ovo feeding studies, which caused the increase PM weight.

Conclusion

Nicotinamide riboside is a novel vitamin $B_3$ analogue that has not been extensively utilized in poultry production. Because NR increases NAD+ production in tissues, and the siturin-1 protein regulates stem cell activity in response to NAD+ levels, it is possible this is the mechanism by which NR increased PM weight and fiber density. The fact that NR increased PM fiber density and weight could impact the poultry industry yields, product quality, or incidence of myopathies.

Example VI

Objective

The objective of this study was to determine the effects of in ovo injection of nicotinamide riboside (NR) on the time course of broiler embryonic myogenesis. Materials and Methods Egg Procurement, Incubation, and In Ovo Injection Fertilized Cobb 500 broiler eggs (N=247; Cobb Vantress, Siloam Springs, Ark.) were transported to Kansas State University Muscle Biology Laboratory (Manhattan, Kans.), egg weights were recorded, and within each 4 egg strata eggs were randomly assigned to an NR treatment (0 mM, 250 mM, 500 mM, or 1 M NR). After treatment allocation, eggs were put onto trays and placed in a Sportsman 1502 incubator (GQF Manufacturing Company Inc., Savannah, Ga.) set to operate at 37° C. and 40±4% relative humidity. Trays were rotated hourly to reposition eggs and egg weights were recorded daily to determine percentage weight loss with a standard daily weight loss ranging from 0.65% to 0.75%.

At d 10 of incubation, the methods of Gonzalez and Jackson (2020) were followed for treatment administration. Eggs were briefly removed from the incubator and prior to injection, the injection site was cleaned with 70% ethanol. One-hundred milliliters of 0.9% sterile saline was injected into yolk sac of each egg with a 2.54-cm, 20-guage injection needle inserted approximately 1-cm into injection site. The injection site was covered with a 1-cm$^2$ portion of medical tape (Nexcare; 3M, Maplewood, Minn.) and placed back into the incubator under the conditions described above. At d 18 of incubation, egg were removed from their trays, placed in hatching boxes, and the humidity of the incubator was increased to 60±2%.

Harvest and Sample Collection

At three time points, E (i.e., embryonic day 15, day 15 after the beginning of incubation), E19, and 24 hours post-hatching, embryos and chicks were euthanized by exposure to $CO_2$ and decapitation. Crown to rump length (CR), head width and head length were measured by calipers (Traceable Digital Calipers; Fisher Scientific, Pittsburg, Pa.). Head and chest circumference were collected by curling a string around the target area and measuring the length of the curled string by a ruler. Chicks chest were sprayed with 70% ethanol, were skinned to expose the PMM, and chest width and length were measured by calipers. Both sides of the PMM were removed and the left side was weighed, followed by length, width, and thickness measurement collection. Following measurement collection, the left PMM was submerged in optimal cutting temperature tissue freezing medium compound, slowly frozen at −20° C. for 1 h, and stored at −80° C. until cryosectioning. The right side of PMM was stored in a 1.5 ml microcentrifuge tube and stored at −80° C. until NAD+ analysis. At last, the heart and liver of each chick were removed, weighed, and discarded.

Immunohistochemistry and Histology

The methods of Gonzalez and Jackson (2020) were followed for immunohistochemistry analysis. On 2 separate slides, 6 cryosections (10 μm thick) were collected on positively charged slides (Diamond White Glass; Globe Scientific Inc., Paramus, N.J.). Cryosections were incubated in 5% horse serum and 0.2% TritonX-100 in phosphate buffered saline (PBS) for 30 min to block all nonspecific binding sites. Cryosections were incubated for 16 h at 4° C. with a primary antibody solution comprising blocking solution and 1:500 rabbit α-dystrophin (Thermo Scientific, Waltham, Mass.) and 1:2 chicken α-Pax7 antibody (Developmental Studies Hybridoma Bank, Iowa City, Iowa). Cryosections were washed 3 times for 5 min with PBS and incubated for 30 min with 1:1,000 Alexa-Flour 594 goat-anti-rabbit H&L (Life Technologies, Carlsbad, Calif.), 1:1000 Alexa-Flour 488 chicken-anti-mouse IgG1 (Life Technologies), and 1:1,000 Hoescht Dye 33342 (Life technologies) secondary antibodies in blocking solution. After washing in PBS 3 times for 5 min, 5 μL of 9:1 glycerol in PBS was placed on each cryosection and slides were coverslipped for imaging.

The methods of Noel et al. (2016) were followed for succinate dehydrogenase (SDH) staining. Slides were incubated at 37° C. for 1 h in a prewarmed incubation solution containing nitro blue tetrazolium solution, phosphate buffer, and sodium succinate solution. After washing in ultrapure water 3 times for 1 min each, 5 μL of 9:1 glycerol in PBS was placed on each cryosection and they were coverslipped for imaging.

All cryosections were imaged at 200× magnification using a Nikon Eclipse TI-U inverted microscope (Nikon Instruments Inc., Melville, N.Y.). Immunohistochemistry photomicrographs were collected with a DS-QiMC digital camera (Nikon Instruments Inc.) and SDH cryosections were collected with a Nikon DS-Fil color digital camera (Nikon Instruments Inc.) White light intensity was kept constant for SDH photomicrographs. All photomicrograph collection and image analyses were conducted using NIS Elements Basic Software (Nikon Instruments Inc.). Cross-sectional area (CSA) of a minimum of 1,000 muscle fibers per chick was determined as the area within the dystrophin border. The number of satellite cell was determined as nuclei co-staining for Pax 7 and Hoechst dye located at the periphery of muscle fiber. A minimum of 50 muscle fiber bundles per chick were analyzed for SDH mean intensity using the same software. The scale for mean intensity ranged from 0 (black or the most intense staining) to 250 (white or the least intense staining).

NAD+ Quantification extractions yielding RNA with a ratio greater than 1.9 were used for real-time PCR analysis. Trace genomic DNA contamination and reverse transcription were conducted on 50 ng of total RNA using a High-Capacity cDNA Reverse Transcription Kit (Life Technologies). Gene specific primers were designed, efficiencies determined, and validated for qPCR (Table 7). Complementary DNA was amplified in duplicate for each sample using PerfeCTa SYBR Green FastMix (Quanta Biosciences, Gaithersburg, Md.) and the appropriate gene specific forward and reverse primers (20 pM) in an Eppendorf Mastercycler realplex2 S PCR System (Eppendorf North America, Hauppauge, N.Y.). Thermal cycling parameters were initial heating at 50° C. for 2 min, denaturing at 95° C. for 10 min, 50 cycles of 15 s at 95.0° C., annealing at 60.5° C. for 30 s, and extension for 20 s at 68.0° C. A final dissociation step was included at 95° C. for 15 s, 60° C. for 30 s, and 95° C. for 15 s. Expression was normalized to 18S ribosomal RNA expression (ΔCt, where Ct refers to the threshold cycle), and calibrated to control chick (0 mM) mRNA expression (ΔΔCt). Gene fold change expression levels were calculated as $2^{-\Delta\Delta Ct}$ as previously described by Livak and Schmittgen (2001).

TABLE 7

| | Gene specific primers utilized for real-time PCR analysis | | | | |
|---|---|---|---|---|---|
| Gene | Forward primer (5' to 3') | Reverse primer (5' to 3') | Tm[1], °C. | Amplicon length, bp | Efficiency |
| Cyclin | | | | | |
| D1 | GCTACCTGCATGTTTGTGGC (SEQ ID NO: 1) | GGGTCTGATGGAGTTGTCGG (SEQ ID NO: 2) | 64 | 92 | 93 |
| D2 | TGAGAACTGCCCTGCTCTTG (SEQ ID NO: 3) | CAGAGGACCTAGCAGCCAAC (SEQ ID NO: 4) | 64 | 84 | 92 |
| D3 | CAGAACTTGCTGAGCCAGGA (SEQ ID NO: 5) | TCCGCATGTAGGGCTTGATC (SEQ ID NO: 6) | 64 | 87 | 97 |
| 18S rRNA[2] | GAACGAGACTCTGGCATGCT (SEQ ID NO: 7) | TCAATCTCGGGTGGCTGAAC (SEQ ID NO: 8) | 64 | 96 | 90 |

[1]Melting temperature.
[2]Normalizing gene. Expression was not affected by treatment.

Nicotinamide adenine dinucleotide content of the right PMM was quantified using a commercial NAD/NADH assay kit (Abnova, Taipei, Taiwan). Twenty-milligram of PMM tissue was homogenized in a propriety NAD extraction buffer, heated at 60° C. for 5 min, and propriety assay and NADH buffers were added. Samples were centrifuged at 14,000 rpm for 5 min and the supernatant was used for analysis. Standards, samples, and working reagent [propriety assay buffer, enzymes, lactate, and 3-(4,5-dimethylthiazol-2-yl)-2,5-diphenyltetrazolium bromide] were loaded onto 96-well plates and absorbance was read at 565 nm at 0 and 15 min. The change in absorbance was used to calculate amount of NAD+.

Cyclin D mRNA Expression

The methods of Burnett et al. (2016) were followed with minor modifications. Briefly, nucleic acids were extracted and purified from 200 mg of the left biceps femoris muscle using Trizol (Life Technologies), followed by subjecting the nucleic acids to PureLink™ RNA Mini Kit (Life Technologies, Carlsbad, Calif.). Total RNA concentration and 260 nm/280 nm ratio were quantified and Statistics All data were analyzed as a completely randomized design with embryo/chick as the experimental unit. Treatment served as the fixed effect and all models were analyzed using the Mixed procedure of SAS 9.4 (SAS Inst. Inc., Cary, N.C.). Pairwise comparisons between the least squares means of the factor level comparisons were computed using the PDIFF option of the LSMEANS statement. Statistical significance was determined at P<0.05.

Results

Body Morphometrics and Muscle Characteristics

There were no treatment effects for all measures collected on E15 embryos (P>0.22; Table 8). Treatment did not affect all whole-body measurements (P>0.08) for E19 embryos with the exception of head circumference (P=0.04; Table 9). Embryos injected with 500 mM and 1 M NR had larger head circumferences than 0 mM embryos (P<0.05), but did not differ (P=0.83) from each other. Embryos injected with 250 mM NR had smaller (P=0.04) head circumferences than 1 M embryos, but did not differ from all other treatments (P>0.07). Treatment did not affect PMM measures (P>0.12), except PMM weight and length (P<0.01). Embryos injected with NR had greater PMM weight and length compared to control embryos (P<0.01), but did not differ from each other (P>0.25).

TABLE 8

Body and pectoralis major morphometrics of E15 embryos injected in ovo at d 10 of embryogenesis with increasing doses of nicotinamide riboside

| | Nicotinamide riboside dose, mM | | | | | |
|---|---|---|---|---|---|---|
| | 0 | 250 | 500 | 1,000 | SEM | P-value |
| Body measurements | | | | | | |
| Weight, g | 13.6 | 14.5 | 14.2 | 13.9 | 0.86 | 0.90 |
| Dimensions, mm | | | | | | |
| Crown-rump length | 59.4 | 61.4 | 61.1 | 61.0 | 1.5 | 0.75 |
| Head width | 13.6 | 13.7 | 13.7 | 14.0 | 0.3 | 0.73 |
| Head length | 17.1 | 17.6 | 17.8 | 17.4 | 0.9 | 0.93 |
| Heart weight, g | 0.13 | 0.14 | 0.13 | 0.14 | 0.01 | 0.23 |
| Liver weight, g | 0.27 | 0.27 | 0.25 | 0.28 | 0.02 | 0.68 |
| Pectoralis major measurements | | | | | | |
| Weight, g | 0.73 | 0.81 | 0.82 | 0.84 | 0.06 | 0.60 |
| Dimensions, mm | | | | | | |
| Length | 17.6 | 18.3 | 17.8 | 18.5 | 0.7 | 0.77 |
| Width | 13.7 | 14.7 | 15.2 | 14.9 | 0.5 | 0.22 |
| Depth | 6.9 | 7.2 | 7.1 | 6.6 | 0.2 | 0.35 |

TABLE 9

Body and pectoralis major morphometrics of E19 embryos injected in ovo at d 10 of embryogenesis with increasing doses of nicotinamide riboside

| | Nicotinamide riboside dose, mM | | | | | |
|---|---|---|---|---|---|---|
| | 0 | 250 | 500 | 1,000 | SEM | P-value |
| Body measurements | | | | | | |
| Weight, g | 37.9 | 37.7 | 37.9 | 38.1 | 1.42 | 1.00 |
| Dimensions, mm | | | | | | |
| Crown-rump length | 85.0 | 84.3 | 85.9 | 86.3 | 0.6 | 0.08 |
| Head width | 17.0 | 15.4 | 15.3 | 15.4 | 0.8 | 0.34 |
| Head length | 17.8 | 17.7 | 17.4 | 17.6 | 0.2 | 0.49 |
| Head circumference | 53.0[a] | 53.2[a,c] | 54.8[b,c] | 55.0[b] | 0.1 | 0.04 |
| Chest circumference | 57.0 | 59.5 | 60.1 | 61.5 | 0.1 | 0.08 |
| Chest length | 18.3 | 18.6 | 18.5 | 18.3 | 0.3 | 0.89 |
| Chest width | 15.6 | 15.5 | 16.3 | 15.4 | 0.3 | 0.14 |
| Heart weight, g | 0.22 | 0.22 | 0.22 | 0.23 | 0.01 | 0.56 |
| Liver weight, g | 0.63 | 0.64 | 0.64 | 0.63 | 0.02 | 0.98 |
| Pectoralis major measurements | | | | | | |
| Weight, g | 0.14[a] | 0.17[b] | 0.18[b] | 0.17[b] | 0.01 | <0.01 |
| Dimensions, mm | | | | | | |
| Length | 15.1[a] | 17.2[b] | 17.7[b] | 17.6[b] | 0.4 | <0.01 |
| Width | 5.1 | 5.5 | 5.7 | 5.6 | 0.2 | 0.12 |
| Depth | 2.7 | 2.9 | 2.7 | 2.9 | 0.1 | 0.29 |

[a,b,c]Treatments with different superscripts within a row differ (P <0.05).

There were no treatment effects on all d21 chick whole body measures (P>0.08; Table 10), except head length and chest width (P=0.05). Chicks from eggs injected with 250 mM NR had greater head lengths and chest widths than control chicks and chicks from eggs injected with 1 M NR (P<0.03), which did not differ from each other (P>0.54). Head length and chest width from hatched chicks injected with 5.0 mM NR were not different from all other treatments (P>0.10).

TABLE 10

Body and pectoralis major morphometrics of hatched chicks injected in ovo at d 10 of embryogenesis with increasing doses of nicotinamide riboside

| | Nicotinamide riboside dose, mM | | | | | |
|---|---|---|---|---|---|---|
| | 0 | 250 | 500 | 1,000 | SEM | P-value |
| Body measurements | | | | | | |
| Weight, g | 45.3 | 46.9 | 46.1 | 46.6 | 0.61 | 0.16 |
| Dimensions, mm | | | | | | |
| Crown-rump length | 93.2 | 95.4 | 95.0 | 93.0 | 1.0 | 0.16 |
| Head width | 15.6 | 15.5 | 15.7 | 15.5 | 0.2 | 0.83 |
| Head length | $17.8^a$ | $18.7^b$ | $18.2^{a,b}$ | $17.8^a$ | 0.3 | 0.05 |
| Head circumference | 54.7 | 55.7 | 55.6 | 53.9 | 0.1 | 0.17 |
| Chest circumference | 60.9 | 61.2 | 62.5 | 61.4 | 0.1 | 0.42 |
| Chest length | 20.5 | 21.9 | 21.2 | 21.1 | 0.5 | 0.14 |
| Chest width | $15.9^a$ | $17.1^b$ | $16.6^{a,b}$ | $16.1^a$ | 0.3 | 0.05 |
| Heart weight, g | 0.29 | 0.31 | 0.31 | 0.32 | 0.01 | 0.08 |
| Liver weight, g | 0.88 | 0.84 | 0.90 | 0.96 | 0.05 | 0.28 |
| Pectoralis major measurements | | | | | | |
| Weight, g | $0.17^a$ | $0.23^b$ | $0.23^b$ | $0.22^b$ | 0.01 | <0.01 |
| Dimensions, mm | | | | | | |
| Length | $17.6^a$ | $19.9^b$ | $20.3^b$ | $19.1^{a,b}$ | 0.7 | <0.01 |
| Width | $4.6^a$ | $5.5^b$ | $5.6^b$ | $5.4^b$ | 0.2 | <0.01 |
| Depth | $2.8^a$ | $3.1^{a,b}$ | $3.3^b$ | $3.0^a$ | 0.2 | 0.02 |

$^{a,b}$Treatments with different superscripts within a row differ (P <0.05).

In hatched chicks, treatment affected all PMM measures (P<0.02). Chicks from eggs injected with NR had greater PMM weight and width than control chicks (P<0.01), but did not differ from each other (P=0.86). Chicks from eggs injected with 250 and 500 mM NR had longer PMM than control chicks (P<0.01), but did not differ (P=0.63) from each other. Chicks from eggs injected with 1 M NR did not differ in PMM length compared to all other treatments (P>0.06). Chicks from eggs injected with 500 mM NR had greater PMM depth than control and 1M chicks (P<0.04), which did not differ (P=0.24) from each other. Chicks from eggs injected with 250 mM NR did not differ in PMM length compared to all other treatments (P>0.06).

Muscle Fiber Morphometrics and Satellite Cell Content

Figure 16:
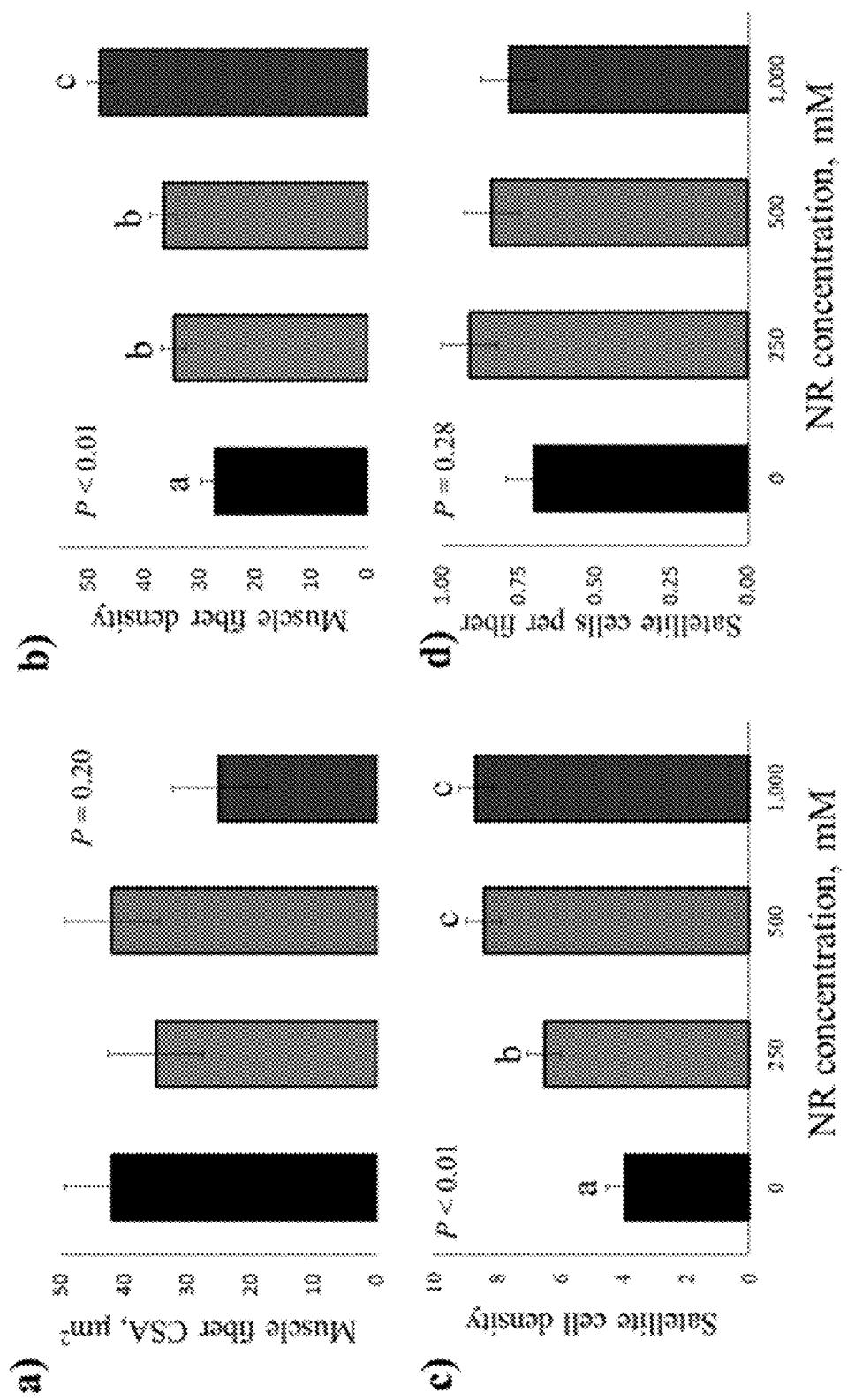
FIG. 16 is a series of graphs showing pectoralis major muscle fiber CSA (a), muscle fiber density (b), satellite cell density (c), and satellite cells per fiber (d), at different nicotinamide riboside treatment concentrations ($^{a,b}$Means with different superscripts differ (P<0.05)

There was no treatment effect (P=0.20) for muscle fiber CSA; however, there was a treatment effect (P<0.01) for muscle fiber density (FIG. 16). Chicks from eggs injected with 1 M NR had greater muscle fiber density than all other treatments (P<0.01). Chicks from eggs injected with 250 and 500 mM NR had greater muscle fiber density than control chicks (P<0.01), but did not differ (P<0.06) from each other.

There was a treatment effect (P<0.01) for satellite cell density from hatched chicks, but there was no treatment effect (P=0.28) for number of satellite cells per muscle fiber. Chicks from eggs injected with 500 mM or 1 M NR had a greater satellite cell density than chicks from the other two treatments (P<0.01), but did not differ (P=0.69) from each other. Chicks from eggs injected with 250 mM NR had a greater (P<0.01) satellite cell density than control chicks.

Succinate Dehydrogenase Staining Intensity and $NAD^+$ Content

Figure 17:
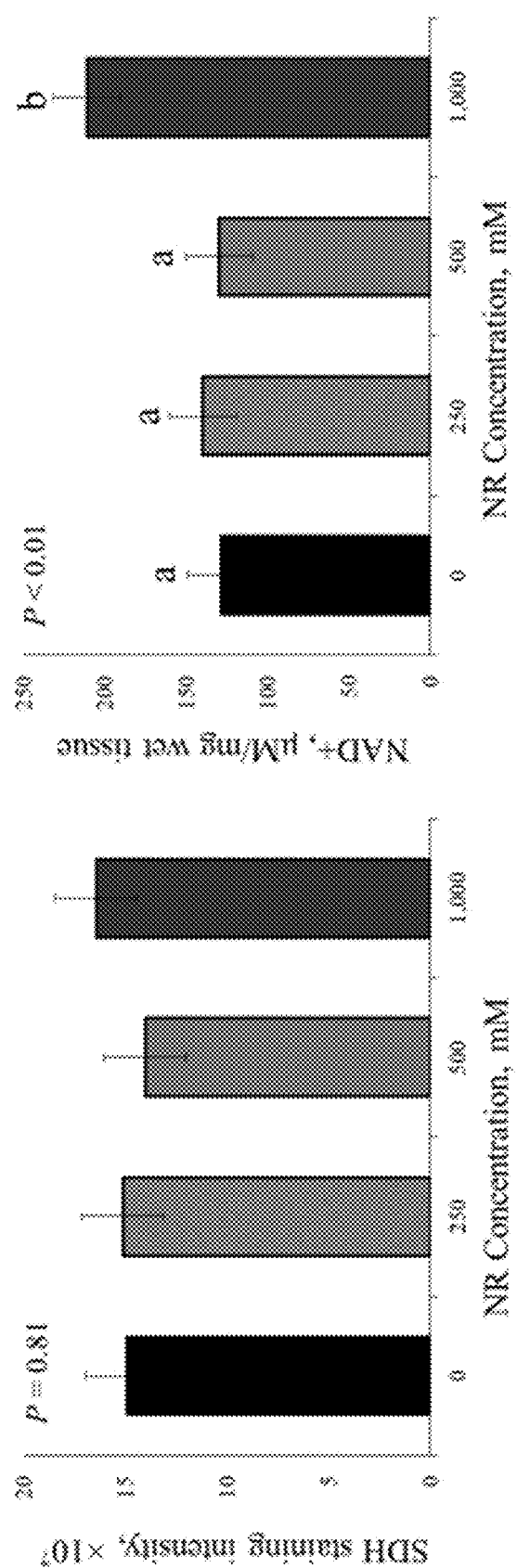
FIG. 17 is a set of graphs showing pectoralis major muscle SDH staining intensity and NAD+ at different nicotinamide riboside treatment concentrations.

There was no treatment effect (P>0.81) for SDH staining intensity on hatched chicks, but there was a treatment effect (P<0.01) for $NAD^+$ content of PMM (FIG. 17). Hatched chicks injected with 1,000 mM NR had more $NAD^+$ than the other 3 treatment groups (P<0.01), which did not differ from each other (P>0.69).

Cyclin D mRNA Expression

Figure 18:
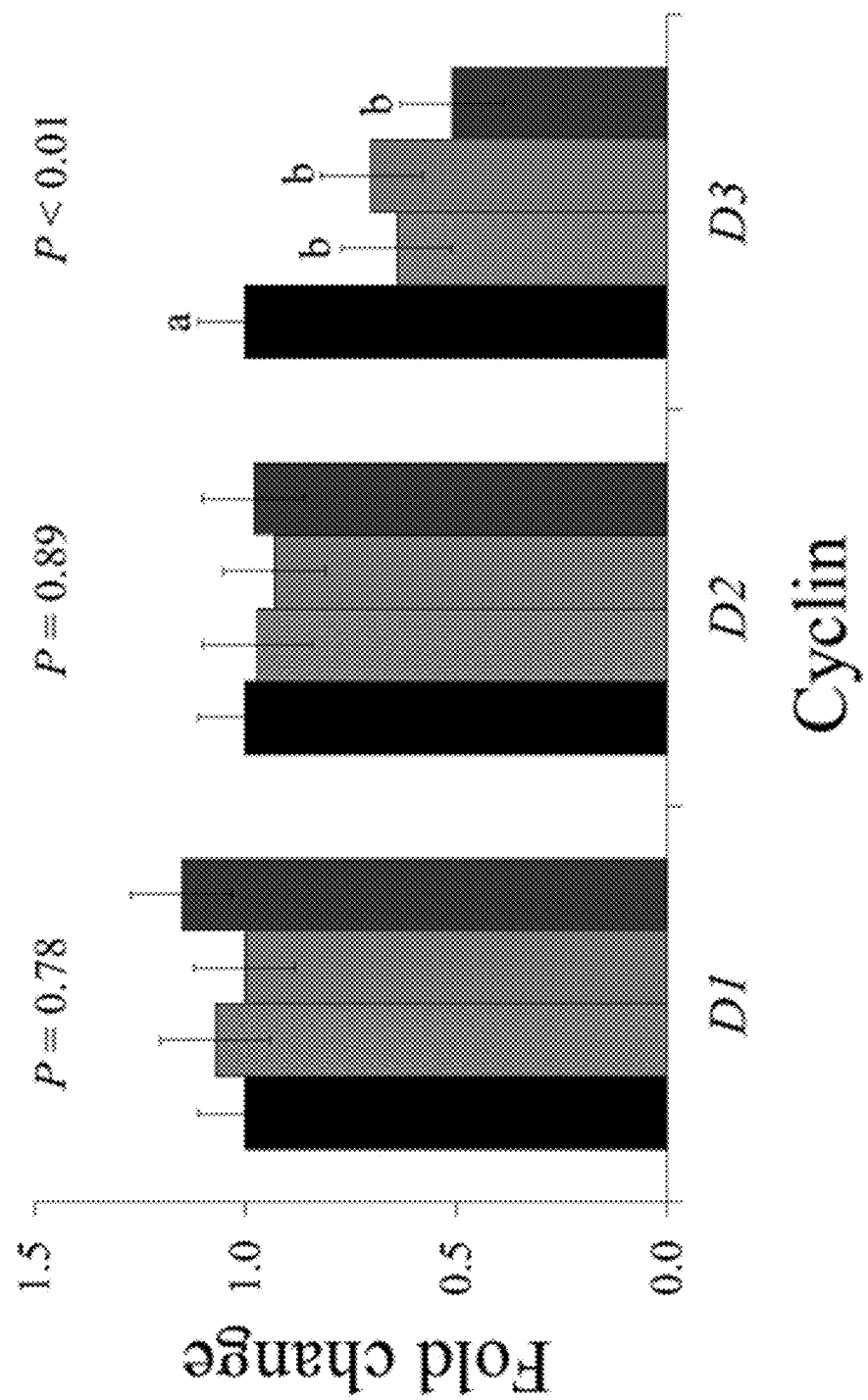
FIG. 18 is a graph showing pectoralis major muscle cell cycle gene fold change expression levels using different nicotinamide riboside treatment concentrations.

There were no treatment effects for cyclin D1 and 2 mRNA expression (P>0.76); however treatment did affect (P=0.01) cyclin D3 expression. Control chicks had greater cyclin D3 expression than all NR treatments (P<0.04), which did not differ from each other (P>0.26). See FIG. 18.

Discussion

From 1925 through 2019, the poultry industry increased broiler market weight by 153% while improving feed efficiency 61%. Equally impressive, birds now reach market weight in 58% less time. Advancements in genetics and nutrition that maximize muscle development and growth are the main factors for these advancements in production efficiency. Despite these production efficiency improvements, the poultry industry is constantly looking to improve growth and muscle deposition in its birds utilizing novel methods. In ovo feeding of nutrients constitutes one such method.

In ovo feeding is defined as direct administration of a compound into eggs during incubation. When used for growth purposes, in ovo injection of compounds appears to affect body weight in a compound dependent manner. In the current study, NR did not affect body weight during embryo development and at hatching; however, head circumference was affected by NR at E19 and head length and chest width were affected at hatching. These improvements contrast the previous study where injecting 250 mM of NR into the albumen or yolk sac of the developing embryo did not affect all whole-body measures. The larger head measurements could signal advancements in brain development; however, the fact other measures were not affected, the affected measurements occurred inconsistently by dose, and the magnitude of the improvements were small, indicated these improvements may not be biologically significant. Because the chest width measurement was taken without the skin and feathers, improvement in the 250 mM treatment may indicate there was increased muscling on the carcasses of those chicks. Previously, injecting 250 mM of NR into the egg of the developing embryo increased PMM weight by 38% and length, width, and depth by 21, 9, and 10%, respectively. In the aforementioned study, measurements were only collected at hatch; however, the current study collected PMM data 2 times before hatching. At E15, NR had no effect on PMM measures, but by E19 NR increased NR increased weight and length by a minimum of 21 and 13%, respectively. At hatch, NR increased the weight advantage to 35% and maintained the 13% increase in PMM length. Therefore, the additional weight may have been due to the 17 and 18% increase in PMM width and depth, respectively. The 250 mM NR response of the current study is similar in magnitude compared to the previous study response, and they also indicate injecting more than 250 mM of NR does not provide any extra benefit for global PMM morphometrics.

With in ovo injections occurring on d 10 of incubation, NR affected the events associated with secondary muscle fiber development. NR injections did not affect muscle fiber CSA, but did increase muscle fiber density. Unlike the global PMM response, injecting 250 and 500 mM NR increased muscle fiber density by an average of 34% compared to control chicks, while 1 M injections increased density by 75%. The 1 M maximum response is the greatest response of the two NR broiler studies and is also greater than other studies injecting various compounds into duck and chickens. These results imply the increase in PMM morphometrics may have been due to the development of more muscle fibers during secondary myogenesis.

Embryonic muscle development involves the proliferation and differentiation of somitic progenitor cells into myoblasts, which terminally differentiate and fuse into myotubes. Satellite cells, the resident muscle stem cell pool responsible for adult muscle growth and repair, originate from Pax7 expressing myogenic progenitor cells in the dermomyotome central domain. The literature does not contain studies documenting the effects of NR supplementation on embryonic and fetal myogenesis. In the current study, the increase in muscle fiber density was also accompanied by an increase in satellite cell density. At hatching, chicks from eggs injected with 250 mM NR had satellite cell density increase by 73% compared to control, and 500 mM and 1 M chicks had an average density increase of 116%. When put on a fiber basis, the NR treatment effect on satellite cell number was eliminated, indicating the increase in density was primarily due to more muscle fibers being formed. More interesting, NAD+ levels were only greater in 1 M chicks, which may be the reason why these chicks had a much greater muscle fiber density than the other treatments. Additionally, the lack of a NR effect on SDH staining intensity indicates there was not a increase in mitochondria biogenesis and the increase in NAD+ level was due to a rise in the efficiency of production.

The cyclins and their dependent kinases serve as regulatory subunits that regulate cell cycle progression. The type D cyclins (D1, D2, and D3) act as unique cell cycle components that sense mitogenic elements in the extracellular environment to increase proliferation. In developing skeletal muscle, myoblast cyclin D1 content increased to prevent terminal differentiation. In the current study, control chicks had greater cyclin D3 mRNA expression by an average of 38%. With cyclin D1 and 2 mRNA expression unchanged, this may indicate control chicks were farther behind in myogenesis compared to NR chicks and were continuing to form myotubes.

Conclusion

In ovo feeding of NR increased PMM morphometrics of E19 of embryos and hatched chicks. Similar to the previous NR in ovo feeding study, increased PMM measurements coincided with an increase in muscle fiber density and no effect on fiber CSA in hatched chicks. While increasing the dose of injected NR did not affect hatched chick PMM morphometrics, dose increased muscle fiber and satellite cell density. The lack of additional PMM development and growth due to NR administration would indicated there is no advantage injecting more than 250 mM of NR; however, the drastic increase is muscle fiber density due to elevating the dose may have implications for future growth or meat quality characteristics.

The invention claimed is:

1. A method of increasing meat quantity and/or improving meat quality in a domesticated meat animal, the method comprising providing to the domesticated meat animal or to an embryo of the domesticated meat animal an effective amount of nicotinamide riboside, wherein the nicotinamide riboside is provided as nicotinamide riboside chloride, nicotinamide riboside sulfate, or combined with amino acid complexes.

2. The method of claim 1, wherein the nicotinamide riboside is provided as nicotinamide riboside chloride.

3. The method of claim 1, wherein the domesticated meat animal is a chicken or a pig.

4. The method of claim 3, wherein the meat animal is a chicken.

5. The method of claim 4, wherein the providing comprises injecting a quantity of nicotinamide riboside into a fertilized chicken egg.

6. The method of claim 5, wherein nicotinamide riboside is injected into the chicken egg at a concentration of at least about 250 mM in about 1 µl to about 1,000 µl of solution.

7. The method of claim 5, wherein the nicotinamide riboside is injected into a yolk of the chicken egg.

8. The method of claim 3, wherein the meat animal is a pig.

9. The method of claim 8, wherein the providing comprises orally administering a quantity of nicotinamide riboside to the pig.

10. The method of claim 8, wherein the nicotinamide riboside is administered at a dose of at least about 15 mg per kg of body weight daily.

11. The method of claim 8, wherein the nicotinamide riboside is administered at a dose of at about 15 mg per kg of body weight to about 30 mg per kg of body weight daily.

12. The method of claim 11, wherein the nicotinamide riboside is administered at a dose of about 30 mg per kg of body weight daily.

13. The method of claim 5, wherein nicotinamide riboside is injected into the chicken egg at a concentration of about 250 mM to about 1,000 mM in about 1 µl to about 1,000 µl of solution.

14. The method of claim 5, wherein the nicotinamide riboside is injected into the chicken egg at a depth of about 0.5 cm to about 2 cm.

15. The method of claim 5, wherein the nicotinamide riboside is injected into the chicken egg about 10 to about 12 days after the chicken egg is laid.

16. A method of increasing meat quantity and/or improving meat quality in a chicken, the method comprising injecting a quantity of nicotinamide riboside into a fertilized chicken egg.

17. The method of claim 16, wherein nicotinamide riboside is injected into the chicken egg at a concentration of at least about 250 mM in about 1 µl to about 1,000 µl of solution.

18. The method of claim 16, wherein the nicotinamide riboside is injected into a yolk of the chicken egg.

19. The method of claim 16, wherein nicotinamide riboside is injected into the chicken egg at a concentration of about 250 mM to about 1,000 mM in about 1 µl to about 1,000 µl of solution.

20. The method of claim 16, wherein the nicotinamide riboside is injected into the chicken egg at a depth of about 0.5 cm to about 2 cm.

21. The method of claim 16, wherein the nicotinamide riboside is injected into the chicken egg about 10 to about 12 days after the chicken egg is laid.

22. The method of claim 16, wherein the nicotinamide riboside is provided as nicotinamide riboside chloride.

23. A method of improving meat quality in a pig, the method comprising orally administering nicotinamide riboside to the pig a dose of at least about 15 mg per kg of body weight daily for at least 7 days, wherein after the administering for at least 7 days, the pig has one or more of the following characteristics as compared to an untreated pig:
    less Longissimus lumborum surface metmyoglobin accumulation;
    less meat visual panelists' surface discoloration;
    more metmyoglobin reducing ability; and/or
    greater NAD+ content.

24. The method of claim 23, wherein the nicotinamide riboside is administered at a dose of about 15 mg per kg of body weight to about 30 mg per kg of body weight daily.

25. The method of claim 23, wherein the nicotinamide riboside is administered at a dose of at least about 30 mg per kg of body weight daily, wherein after the administering for at least 7 days, the pig has one or more of the following characteristics as compared to an untreated pig:
    better average daily gain;
    larger loin eyes; and/or
    increased semitendinosus muscle NAD+ levels.

26. The method of claim 23, wherein the nicotinamide riboside is provided as nicotinamide riboside chloride.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gctacctgca tgtttgtggc                                                  20

<210> SEQ ID NO 2
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 2
gggtctgatg gagttgtcgg                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tgagaactgc cctgctcttg                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cagaggacct agcagccaac                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cagaacttgc tgagccagga                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tccgcatgta gggcttgatc                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gaacgagact ctggcatgct                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
tcaatctcgg gtggctgaac                                                    20
```